United States Patent [19]

Reinehr et al.

[11] Patent Number: 4,460,790

[45] Date of Patent: Jul. 17, 1984

[54] SUBSTITUTED 1,11-DIAMINOUNDECANES, PROCESSES FOR PRODUCING THEM, AND THEIR USE

[75] Inventors: Dieter Reinehr, Kandern, Fed. Rep. of Germany; Josef Pfeifer, Therwil, Switzerland

[73] Assignee: Ciba-Geigy Corporation, Ardsley, N.Y.

[21] Appl. No.: 288,853

[22] Filed: Jul. 31, 1981

Related U.S. Application Data

[63] Continuation of Ser. No. 083,141, Oct. 9, 1979, abandoned.

[30] Foreign Application Priority Data

Oct. 18, 1978 [CH] Switzerland .................. 10770/78

[51] Int. Cl.$^3$ .................. C07C 87/14; C07C 87/32; C07C 87/34; C07C 87/36
[52] U.S. Cl. .................. 564/511; 564/455
[58] Field of Search .................. 564/511, 455

[56] References Cited

U.S. PATENT DOCUMENTS

| | | | |
|---|---|---|---|
| 3,145,193 | 8/1964 | Gabler | 260/78 |
| 3,150,117 | 9/1964 | Gabler | 260/78 |
| 3,563,959 | 2/1971 | Schade et al. | 564/511 |
| 3,597,400 | 8/1971 | Kashiro et al. | 260/78 |
| 3,706,802 | 12/1972 | Arrigo | 260/566 F |
| 3,939,147 | 2/1976 | Hugelin et al. | 260/239 BC |
| 4,100,111 | 7/1978 | Peter et al. | 564/511 |

FOREIGN PATENT DOCUMENTS

| | | | |
|---|---|---|---|
| 1520908 | 8/1960 | Fed. Rep. of Germany | 564/511 |
| 1251520 | of 1971 | United Kingdom | 564/511 |
| 1377887 | 12/1974 | United Kingdom | 564/511 |
| 1548431 | 7/1979 | United Kingdom | 564/511 |

OTHER PUBLICATIONS

Wender et al., "J. Org. Chem.", 43, pp. 782–784, (1978).
Reinehr, "Helu. Chim. Acta.", 61, pp. 3, 1122–1124, (1978).
Worley et al., "Tetrahedron", 34, pp. 833–839, (1978).
Clark et al., "Chem. Abs.", 37, #6275$^6$, (1943).
Haser et al., "J. Org. Chem.", 26, pp. 1822–1825, (1961).

*Primary Examiner*—Paul F. Shaver
*Attorney, Agent, or Firm*—Luther A. R. Hall

[57] ABSTRACT

There are described novel substituted 1,11-diaminoundecanes, particularly those of the formula

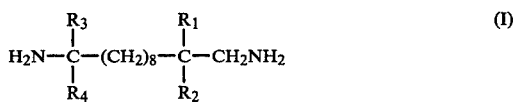

[$R_1$ is alkyl having 1–12 C atoms, $R_2$ is hydrogen or alkyl having 1–12 C atoms, $R_3$ is alkyl having 1–12 C atoms, cycloalkyl having 4–12 C atoms, aralkyl having 7 or 8 C atoms, unsubstituted or substituted aryl, pyridyl, furyl or thienyl, $R_4$ is hydrogen, alkyl having 1–12 C atoms, cycloalkyl having 4–12 C atoms, or unsubstituted or substituted aryl, or $R_1$ and $R_2$ and/or $R_3$ and $R_4$ together are alkylene having 3–11 C atoms], and processes for prducing them. The compound of the formula I can be used for example for producing polycondensation products, particularly polyamides. They can be used also as curing agents for epoxide resins.

8 Claims, No Drawings

SUBSTITUTED 1,11-DIAMINOUNDECANES, PROCESSES FOR PRODUCING THEM, AND THEIR USE

This is a continuation of application Ser. No. 083,141 filed on Oct. 9, 1979, now abandoned.

The present invention relates to novel substituted 1,11-diaminoundecanes and to processes for their use.

It is known that unsubstituted or substituted alkylenediamines are suitable for producing transparent polyamides. There are thus described for example in the German Offenlegungsschrift No. 1,720,513 transparent polyamides generically resistant to boiling and formed from aromatic dicarboxylic acids and alkylenediamines which have 1-10 C atoms in the chain and which can be substituted by alkyl, and which on at least one of the two terminal C atoms are substituted by an alkyl group having 1-4 C atoms. The actual disclosure in this Offenlegungsschrift is limited however to transparent polyamides formed from aromatic dicarboxylic acids and alkylenediamines of the aforementioned type having at most 7 C atoms in the chain. In the British patent specifications Nos. 905,475 and 919,096 are described further transparent polyamides formed from terephthalic acid, isophthalic acid, or mixtures thereof, and hexamethylenediamines having at least three C atoms in one or more side chains, which C atoms have been introduced by alkyl substitution, such as 2,2,4- and 2,4,4-trimethylhexamethylenediamine, 2-methyl-4-ethylhexamethylenediamine and 2-ethyl-4-methylhexamethylenediamine, or isomeric mixtures of hexamethylenediamines of this type. Alkylene diamines are suitable also as co-condensation components for producing transparent polyamides from 4,4'-diaminodicyclohexylalkanes and aromatic dicarboxylic acids, and optionally further co-condensation components, such as aminocarboxylic acids or lactams thereof and aliphatic dicarboxylic acids. Polyamides of this kind are described for example in the U.S. Pat. No. 3,597,400, and in the German Offenlegungsschrift No. 2,642,244. These prior known polyamides and copolyamides leave much to be desired however with regard to water absorption, stability to hydrolysis, dimension stability under heat and/or dimensional stability under the action of moisture, in consequence of which also the mechanical and electrical properties of these polyamides are impaired. The stated polyamides are moreover in some cases products which can be thermoplastically processed only with difficulty or are brittle products.

There have now been found novel diamines which are suitable for producing transparent polyamides which are free from the disadvantages mentioned above.

The novel substituted 1,11-diaminoundecanes correspond to the formula I

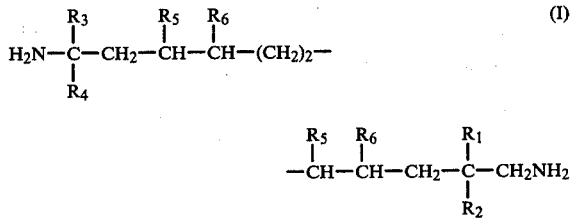

wherein $R_1$ is alkyl having 1-12 C atoms,
$R_2$ is hydrogen or alkyl having 1-12 C atoms,
$R_3$ is alkyl having 1-12 C atoms, cycloalkyl having 4-12 ring C atoms, aralkyl having 7 or 8 C atoms, unsubstituted or substituted aryl, pyridyl, furyl or thienyl,
$R_4$ is hydrogen, alkyl having 1-12 C atoms, cycloalkyl having 4-12 ring C atoms, aralkyl having 7 or 8 C atoms, or unsubstituted or substituted aryl, or
$R_1$ and $R_2$ and/or $R_3$ and $R_4$ together are alkylene having 3-11 C atoms, and
$R_5$ and $R_6$ independently of one another are hydrogen or methyl.

Alkyl groups denoted by $R_1$ to $R_4$ can be straight-chain or branched-chain. Alkyl groups $R_1$, $R_2$ and $R_4$ preferably contain 1-5 C atoms and are straight-chain. Alkyl groups $R_3$ advantageously contain 1-7 C atoms; particularly preferred are branched-chain alkyl groups $R_3$ having 3-7 C atoms. Examples of alkyl groups $R_1$ to $R_4$ are: the methyl, ethyl, n-propyl, isopropyl, n-, sec- and tert-butyl, n-pentyl, 2- or 3-pentyl, n-hexyl, 2- or 3-heptyl, n-octyl, n-decyl and n-dodecyl group.

Cycloalkyl groups $R_3$ and $R_4$ can also be substituted by $C_{1-4}$-alkyl groups. In particular it is cycloalkyl substituted by a methyl or ethyl group. Preferably, however, cycloalkyl groups $R_3$ and $R_4$ are unsubstituted and contain 5-8 ring C atoms. The cyclopentyl and especially the cyclohexyl group are particularly preferred.

Possible aralkyl groups $R_3$ and $R_4$ are especially the benzyl, methylbenzyl or phenylethyl group. If $R_3$ or $R_4$ is substituted aryl, suitable substituents are particularly alkyl groups having 1-4 C atoms and especially 1 or 2 C atoms. Aryl groups $R_3$ and $R_4$ can carry several alkyl groups, but are preferably substituted by only one alkyl group. Particularly preferred are the 1- or 2-naphthyl group, phenyl substituted by an alkyl group having 1-4 C atoms and above all 1 or 2 C atoms, and more especially unsubstituted phenyl.

Suitable pyridyl, furyl or thienyl groups $R_3$ are in particular the pyridyl-3, pyridyl-4, furyl-2 and thienyl-2 groups.

Alkylene groups denoted by $R_1$ and $R_2$ and/or $R_3$ and $R_4$ preferably contain 4-7 C atoms. They are particularly the tetramethylene group and more especially the pentamethylene group.

Preferred compounds of the formula I are those wherein $R_1$ is alkyl having 1-5 C atoms, $R_2$ is hydrogen or alkyl having 1-5 C atoms, or $R_1$ and $R_2$ together are alkylene having 4-7 C atoms, $R_3$ is alkyl having 1-7 C atoms, cycloalkyl having 5-8 C atoms or unsubstituted phenyl, $R_4$ is hydrogen or alkyl having 1-5 C atoms, and $R_5$ and $R_6$ are each hydrogen.

Particularly preferred compounds of the formula I are those wherein $R_1$ is alkyl having 1-5 C atoms, $R_2$ is alkyl having 1-5 C atoms or hydrogen, or $R_1$ and $R_2$ together are alkylene having 4-7 C atoms, $R_3$ is branched-chain alkyl having 3-7 C atoms or cycloalkyl having 5-8 C atoms, $R_4$ is hydrogen, and $R_5$ and $R_6$ are each hydrogen. More especially preferred compounds of the formula I are those wherein $R_1$ and $R_2$ are each methyl or ethyl, or together are $C_{4-7}$-alkylene, particularly pentamethylene, $R_3$ is isopropyl, 3-pentyl, $C_{5-8}$-cycloalkyl, especially cyclohexyl, and $R_4$, $R_5$ and $R_6$ are each hydrogen.

Especially preferred compounds of the formula I according to the invention are those corresponding to the formulae IX to XI:

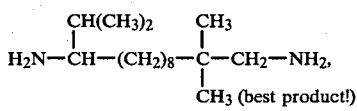

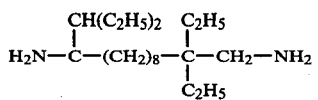

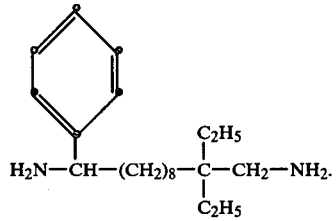

The compounds of the formula I can be produced by either (A) reacting a compound of the formula II

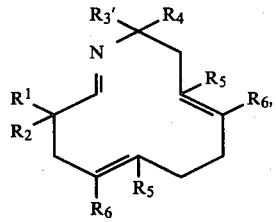

wherein $R_1$, $R_2$ and $R_4$ to $R_6$ have the meanings given under the formula I, and $R_3'$ is the same as $R_3$ under the formula I, or when $R_4$ is hydrogen $R_3'$ is also —CH=CH-alkyl or —C(alkyl)=CH-alkyl having 1-4 C atoms in each of the alkyl moieties,
with a compound of the formula IIIa or IIIb $$H_2N-Y \qquad (IIIa)$$

or $$[H_2N Y \cdot H^\oplus]_n X^{\ominus n} \qquad (IIIb),$$

wherein X is the anion of an inorganic acid not oxidising under the reaction conditions, n is an integer corresponding to the valency of X, and Y is one of the groups

—OH, —NH$_2$, —NH,

-continued

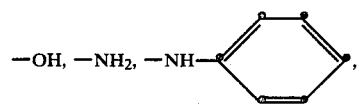—CH$_2$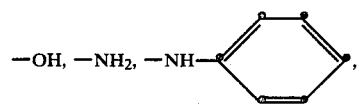 or —NHCONH$_2$, to obtain a compound of the formula IVa

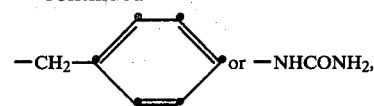

wherein m is the number 1 or 2, and Y' where m is 1 has the above meaning, and where m is 2 it is the direct bond; or (B) catalytically hydrogenating a compound of the formula II to a compound of the formula V

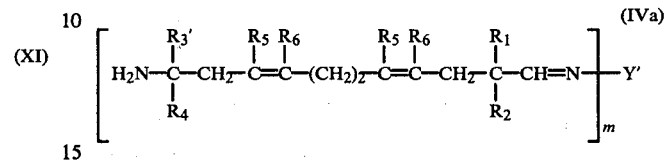

wherein $R_1$ to $R_6$ have the meanings given under the formula I, and reacting the compound of the formula V with one of the compounds of the formula IIIa or IIIb to give a compound of the formula IVb

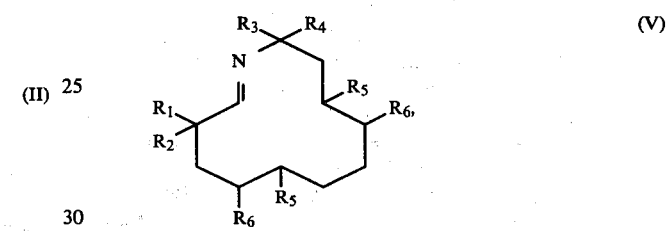

in which m and Y' have the meanings given under the formula IVa, and catalytically hydrogenating the compound of the formula IVa or IVb to obtain a compound of the formula I.

If $R_3'$ is a group —CH=CH-methyl or —C(alkyl)=CH-alkyl, the alkyl moieties in these groups are preferably straight-chain, and are particularly methyl or ethyl.

Intermediates of the formula IVb can also be obtained by catalytic hydrogenation of compounds of the formula IVa. The preferred method of production of compounds of the formula IVb is however that described under (B).

The reaction of 1-aza-1,5,9-cyclododecatrienes of the formula II and of 1-aza-cyclododecenes of the formula V with the compounds of the formula IIIa or IIIb is advantageously performed in an aqueous medium at temperatures of between about 20° and 100° C. X is for example the anion of hydrochloric or hydrobromic acid, or of sulfuric or phosphoric acid. The compound of the formula IIIb preferably used is hydroxylamine hydrochloride, hydroxylamine sulfate or hydroxylamine hydrogen sulfate.

The compounds of the formulae II and V are advantageously used in essentially stoichiometric amounts, relative to the compounds of the formula IIIa or IIIb. It is of advantage however to use a slight excess of compounds of the formula IIIa or IIIb.

There can be formed by the above reactions intermediate compounds of the formula VIa or VIb The catalysts used can be hydrogenation catalysts known per se, such as platinum, rhodium, palladium and ruthenium catalysts. Rodium/aluminium oxide catalysts or palladium/charcoal catalysts are preferably used for hydrogenation of 1-aza-1,5,9-cyclododecatrienes. The

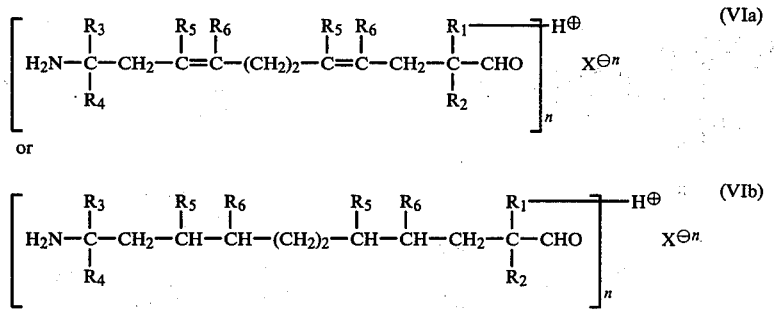

wherein $R_1$ to $R_6$, X and n have the meanings given in the foregoing.

It is in general advisable to perform the reaction with the addition of an inorganic acid not oxidising under the reaction conditions, such as dilute HCl or sulfuric acid.

After completion of the reaction to the compounds of the formula IVa or IVb, the reaction mixture is advantageously neutralised by the addition of a suitable organic or inorganic base, such as carbonates or hydrogen carbonates of alkali metals or alkaline-earth metals, or tertiary amines, for example triethylamine or pyridine. An alkali metal hydroxide, particularly sodium or potassium hydroxide is preferably used as base.

The catalytic hydrogenation of 1-aza-1,5,9-cyclododecatrienes of the formula II to 1-aza-cyclodo-decenes of the formula V, the catalytic hydrogenation of 11-aminoundeca-4,8-dienal compounds of the formula VIa to 11-aminoundecanal compounds of the formula VIb, and also the hydrogenation of compounds of the formulae IVa and IVb to the diamines of the formula I, can be performed by methods known per se, advantageously in the presence of a suitable inert solvent. The hydrogenation reactions are generally carried out in a closed system under a pressure of about 1 to 200 bars, and especially 1 to 130 bars. The hydrogenation temperatures are in general between about 0° and 150° C., and particularly between about 25° and 100° C.

Examples of suitable inert organic solvents for the hydrogenation reactions are: alcohols having up to 6 C atoms, such as methanol, ethanol, propanol, isopropanol, butanols and pentanols; aliphatic and cycloaliphatic hydrocarbons, such as n-pentane, and n-hexane and cyclohexane; cyclic ethers, such as tetrahydrofuran, tetrahydropyrane and dioxane; ethylene glycol and diethylene glycol mono- and -dialkyl ethers having 1-4 C atoms in each of the alkyl moieties, such as ethylene glycol and diethylene glycol monomethyl and -monoethyl ethers, ethylene glycol and diethylene glycol dimethyl and -diethyl ethers. Preferred solvents for the hydrogenation of 1-aza-1,5,9-cyclododecatrienes of the formula II and for the hydrogenation of compounds of the formula IVa to compounds of the formula VIb are cyclohexane and tetrahydrofuran; whilst for the hydrogenation of compounds of the formula IVa and IVb to the diamines of the formula I the preferred solvent is methanol. This last-mentioned hydrogenation reaction is optionally performed in the presence of liquid ammonia or sodium hydroxide.

preferred catalysts for hydrogenation of compounds of the formulae IVa and IVb to the diamines of the formula I are nickel catalysts, particularly Raney nickel.

Compounds of the formula I wherein $R_3$ and/or $R_4$ are cyclohexyl can also be produced by catalytic hydrogenation of the corresponding compounds of the formula I wherein $R_3$ and/or $R_4$ = phenyl, with catalysts of the aforementioned type, particularly platinum/charcoal, palladium/charcoal or ruthenium/charcoal catalysts, being used. This hydrogenation reaction is advantageously performed in water, in alcohols having up to 6 C atoms, or in water/alcohol mixtures.

The starting products of the formulae IIIa and IIIb are known. The compounds of the formula II can be produced, in a manner analogous to that described in Helv. Chim. Acta, 61, Fasc. 3, 1122–1124 (1978), by nickel-catalysed co-oligomerisation of 2-aza-1,3-butadienes of the formula VII

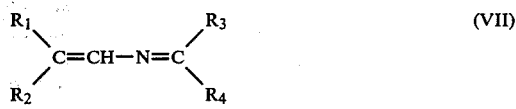

with compounds of the formula VIII

wherein $R_1$ to $R_6$ have the meanings given under the formula I. Suitable catalyst systems are described for example in the German Offenlegungsschrift No. 2,330,087. Preferred catalysts are those which are obtained in situ by reduction of a nickel compound free from carbon monoxide, such as nickel stearate and particularly nickel acetylacetonate, with halogen-free metal arylene or metal alkylene, for example ethoxy-diethylaluminium, in the presence of an alkyl- or arylphosphine, or in the presence of an alkyl- or arylphosphite.

The above reaction is advantageously carried out in the presence of an inert organic solvent, such as n-hexane, n-heptane, benzene, toluene, diethyl ether or dioxane, at temperatures between about −40° C. and +150° C.

The 2-aza-1,3-butadienes of the formula VII are for the most part known, or can be produced for example as follows:

by reaction of aldehydes $R_3$—CHO or ketones

with alkenylamines $H_2N$—$CH_2$—$C(R_1')$=$CH$—$R_2'$ [$R_1'$=H or alkyl having 1–12 C atoms, $R_2'$=H or alkyl having 1–11 C atoms], and subsequent isomerisation of the resulting compounds $R_2'$—$CH$=$C(R_1')$—$CH_2$—$N$=$C(R_3)(R_4)$ in the presence of catalysts, such as $K_2O/Al_2O_3$ catalysts, alkali metal alcoholates or alkaline-earth metal alcoholates [see for example B. A. Kazanskii et al., Zhurnal Organicheskoi Khimii, 6, No. 11,2197–99 (1970), or Akad. Nauk SSSR, Ser.Khim., No. 9,2038–2045 (1975) and Tetrahedron, 34, 833–839 (1978)];

by reaction of allylamine or methylallylamine with aldehydes $(R_1)(R_2'')$—$CH$—$CHO$ [$R_2''$ as $R_2$, but is not H], and subsequent isomerisation of the resulting compounds $(R_1)(R_2'')$—$CH$—$CH$=$N$—$CH_2$—$C(R)$=$CH_2$ [R=H or methyl], in the presence of catalysts, such as potassium tert-butylate;

by reaction of aldehydes $R_1CH(R_2'')$—$CHO$ [$R_2''$ is as $R_2$, but is not H] with ammonia (see for example U.S. Pat. No. 2,319,848), and eventual further reaction of the resulting compounds $(R_1)(R_2'')$—$C$=$CH$—$N$=$CH$—$CH(R_2'')(R_1)$ with suitable ketones or aldehydes (see for example U.S. Pat. No. 3,706,802).

After completion of the reaction and removal of the catalysts and the solvent, the diamines of the formula I can be isolated and purified in the customary manner, for example by distillation.

Essentially, the diamines of the formula I can also be produced from 1-aza-1,5,9-cyclododecatrienes (or -dodecenes) (single-vessel process) by treating them firstly with an acid not oxidising under the reaction conditions (for example HCl or sulfuric acid), and subsequently catalytically hydrogenating in the presence of liquid ammonia. There are intermediately formed in this process compounds of the formula IVa or IVb wherein Y is H and m is 1.

The diamines of the formula I can be used for example for producing polycondensation products, especially polyamides. Transparent polyamides obtained by polycondensation of diamines of the formula I, wherein $R_3 \neq$ heterocyclic radical, with aromatic dicarboxylic acids, particularly terephthalic acid and/or isophthalic acid, and optionally further diamines and aliphatic dicarboxylic acids, are characterised by high glass transition temperatures and accordingly by high dimensional stability under heat, by good thermoplastic processing characteristics, for example in the injection moulding process or extrusion process, by low water absorption combined with reduced dependence of the mechanical and electrical properties on the surrounding moisture, and by improved stability to hydrolysis and resistance to boiling water.

Further subject matter of the invention is also the use of the diamines according to the invention as curing agents for epoxide resins. The corresponding curable mixtures according to the invention contain (a) a diamine of the formula I, and
(b) a polyepoxide compound (X) having on average more than one epoxide group in the molecule, there being in the mixtures, to 1 equivalent of epoxide groups of the epoxide compound (X), 0.5 to 1.5 equivalents of active hydrogen atoms, which are bound to nitrogen, of the respective diamine of the formula I.

The diamines usable as curing agents can also be used in the form of an adduct curing agent (E) which has an amine number of 3 to 7 gram equivalents/kg and is formed from the diamine of the formula I and a liquid epoxide compound (Z) having an average more than one epoxide group in the molecule. Phenylglycide is optionally used. In the mixtures there are, to 1 equivalent of epoxide groups of the epoxide compound (X), 0.8 to 1.2 equivalents of active hydrogen atoms bound to the nitrogen atoms of the adduct curing agent (E).

There can essentially be used also only one epoxide resin, that is to say, base resin (X) and the epoxide resin (Z) contained in the adduct curing agent (E) are the same compound.

The curable mixtures according to the invention have the advantages that their pot life is long, and that they result in products of high flexibility. Furthermore, there is obtained excellent adhesion when they are used as adhesives and lacquers.

The invention is further illustrated in the following Examples. Except where otherwise expressly stated, the term 'parts' denotes parts by weight.

EXAMPLE 1

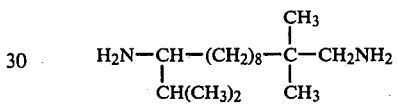

(a) 2.57 g (0.01 mol) of nickel acetylacetonate and 1.66 g (0.01 mol) of triethyl phosphite are dissolved in 120 g of absolute toluene under protective gas (argon), whereupon the solution is saturated at 20°–25° C. with 1,3-butadiene. There is subsequently slowly added dropwise, whilst a gentle flow of 1,3-butadiene is being introduced, 3.9 g (0.03 mol) of ethoxy-diethylaluminium. The mixture is heated to 60° C. and, as a strong stream of 1,3-butadiene is being fed in, 122.5 g (0.98 mol) of N-isobutylidene-2-methylpropenylamine [produced by reaction of isobutyraldehyde with ammonia according to J. Org. Chem., 26, 1822–25 (1961)] is added dropwise, within 45 minutes, in such a manner that the introduced butadiene is exactly used up. After completion of the dropwise addition, stirring is maintained for one further hour at 60° C., with the continuous feeding in of 1,3-butadiene, and the temperature is then lowered to 20°–25° C. The catalyst is inactivated by the addition of 0.32 g (0.01 mol) of sulfur, and the reaction solution is distilled. Subsequent fine distillation yields 212.5 g (0.912 mol) of 3,3-dimethyl-12-isopropyl-1-aza-1,5,9-cyclododecatriene; b.p. 54°–55° C./1.33 Pa; $n_D^{20}$=1.4832.

(b) 233.4 g (1 mol) of 3,3-dimethyl-12-isopropyl-1-aza-1,5,9-cyclododecatriene is added dropwise to 100 g of 37% hydrochloric acid and 200 ml of water in the course of 1 hour, in a manner ensuring that the temperature does not exceed 80° C. The mixture is then cooled to 20°–25° C., and 69.5 g (1.0 mol) of hydroxylamine hydrochloride is added. There is subsequently added during one hour, with water-bath cooling, about 92 g (2.3 mols) of solid sodium hydroxide until the pH value of the aqueous solution is 10–11. The organic phase which precipitates is separated, and washed free from salt with water. Distillation yields 245 g (0.92 mol) of 2,2-dimethyl-11-isopropyl-11-amino-undeca-4,8-dienal-oxime; b.p. 158°–162° C./4 Pa; $n_D^{20} = 1.4930$.

(c) 490 g (1.84 mols) of 2,2-dimethyl-11-isopropyl-11-amino-undeca-4,8-dienal-oxime is dissolved in 2.4 liters of methanol, and the solution is transferred, together with about 200 g of liquid ammonia, with the addition of 150 g of Raney nickel, to a 6.3-liter steel autoclave. Hydrogen is subsequently injected up to a pressure of 100 bars, and the temperature is raised to 100° C. with stirring. Hydrogenation is performed for about 5 hours under these conditions; the mixture is then cooled, and the ammonia and excess hydrogen are released. Subsequent distillation under high vacuum yields 436 g (1.705 mols) of 1-isopropyl-10,10-dimethyl-1,11-diaminoundecane in the form of colourless liquid clear as water; yield 92.6% of theory; b.p. 87° C./4 Pa; $n_D^{20} = 1.4619$.

Analysis for $C_{16}H_{36}N_2$ (molecular weight 256.48): calculated: C 74.93%, H 14.15%, N 10.92%, found: C 74.99%, H 14.17%, N 10.79%.

MS spectrum: molecular peak 256, masses of the fragments 241, 227, 213, 196, 184, 128, 72, 56.

H-NMR spectrum $\tau$(ppm): 7.45(m) and 7.52(s), 8.2–8.7(m), 8.92(s) and 9.03(dd) and 9.08(s) in the ratio of 3:17:16.

EXAMPLE 2

(a) 466.8 g (2 mols) of 3,3-dimethyl-12-isopropyl-1-aza-1,5,9-cyclododecatriene is dissolved in 4 liters of cyclohexane, and the solution is hydrogenated at 20°–25° C. under an initial pressure of 100 bars, in the presence of 50 g of rhodium/aluminium oxide, for 4 hours in a steel autoclave. The solvent is then distilled off to obtain as the main fraction, 425 g (1.79 mols) of 3,3-dimethyl-12-isopropyl-1-aza-cyclododecene; b.p. 92°–94° C./4 Pa; $n_D^{20} = 1.4706$.

(b) The procedure is carried out as described in Example 1(b) but with the use of 118.7 g (0.5 mol) of 3,3-dimethyl-12-isopropyl-1-aza-cyclododecene, 35 g (0.5 mol) of hydroxylamine hydrochloride, 55 g of 37% hydrochloric acid, 200 ml of water and 50 g (1.25 mols) of solid sodium hydroxide. Distillation yields 127 g (0.47 mol) of 2,2-dimethyl-11-isopropyl-11-amino-undecanal-oxime; b.p. 145° C./4 Pa; $n_D^{20} = 1.4761$.

(c) The procedure is carried out as described in Example 1(c) but with the use of 221 g (0.819 mol) of 2,2-dimethyl-11-isopropyl-11-amino-undecanal-oxime. There is obtained after distillation 202 g (0.789 mol) of 1-isopropyl-10,10-dimethyl-1,11-diaminoundecane; yield 96.2% of theory.

EXAMPLE 3

(a) In a manner analogous to that described in Example 1(a), 48.5 g (0.437 mol) of N-propylidene-(2-methylpropenylamine [1-ethyl-4,4-dimethyl-2-aza-1,3-butadiene] is reacted with 61.0 g (1.13 mols) of 1,3-butadiene. By distillation is obtained 62.0 g (0.283 mol) of 3,3-dimethyl-12-ethyl-1-aza-1,5,9-cyclododecatriene; b.p. 65°–66° C./0.7 Pa; $n_D^{20} = 1.4864$.

The N-propylidene-(2-methylpropenylamine) was produced as follows: 25 g (0.223 mol) of potassium tert-butylate is suspended in one liter of anhydrous diethyl ether. There is then added dropwise within 1 hour, with continuous stirring, 921 g (8.3 mols) of isobutylidene-allylamine in such a manner that the temperature of the reaction mixture does not exceed 20° C. After the dropwise addition has been completed, stirring is continued at 20°–22° C. for a further 5 hours. The reaction is subsequently interrupted, and the solvent is distilled over at a bath temperature of 40° C./27000–35000 Pa. The residue is distilled, at a bath temperature of 70° C./13 Pa, into a receiver cooled with $CO_2$/methanol. Fine distillation yields 808 g (7.93 mols) of N-propylidene-(2-methylpropenylamine); b.p. 122° C.; $n_D^{20} = 1.471$.

(b) The procedure as described in Example 1(b) is carried out but using in this case 219 g (1 mol) of 3,3-dimethyl-12-ethyl-1-aza-1,5,9-cyclododecatriene, 147 g (1.5 mols) of sulfuric acid and 82 g (0.5 mol) of hydroxylamine sulfate. The yield after processing is 222 g (0.879 mol) of 2,2-dimethyl-11-ethyl-11-amino-undeca-4,8-dienal-oxime in the form of highly viscous liquid; b.p. 162°–164° C./7 Pa.

(c) The procedure is carried out as described in Example 1(c) but with the use of 172.5 g (0.684 mol) of 2,2-dimethyl-11-ethyl-11-amino-undeca-4,8-dienal-oxime. Distillation yields 160 g (0.661 mol) of 1-ethyl-10,10-dimethyl-1,11-diaminoundecane; yield 96.5% of theory; b.p. 93° C./7 Pa; $n_D^{20} = 1.4622$.

Analysis for $C_{15}H_{34}N_2$ (molecular weight 242.45): calculated: C 74.31%, H 14.14%, N 11.56%, found: C 74.35%, H 14.32%, N 11.71%.

MS spectrum: molecular peak 242, masses of the fragments 227, 213, 196, 184, 128, 98, 56.

$^1$H-NMR spectrum $\tau$(ppm): 7.42(m) and 7.58(s), 8.69(m), 8.92(s), 9.08(t) and 9.15(s) in the ratio of 3:18:4:9.

EXAMPLE 4

(a) The procedure is carried out as described in Example 2(a) but with the use of 438 g (2 mols) of 3,3-dimethyl-12-ethyl-1-aza-1,5,9-cyclododecatriene. The yield after distillation is 412 g (1.85 mols) of 3,3-dimethyl-12-ethyl-1-aza-cyclododecene; b.p. 61°–63° C./4 Pa; $n_D^{20} = 1.4721$.

(b) The procedure as described in Example 1(b) is carried out but with the use of 223 g (1 mol) of 3,3-dimethyl-12-ethyl-1-aza-cyclododecene, 82 g (0.5 mol) of hydroxylamine sulfate, 150 g of sulfuric acid and 400 ml of water. Distillation yields 245 g (0.955 mol) of 2,2-dimethyl-11-ethyl-11-amino-undecanal oxime; b.p. 155°–160° C./7 Pa.

(c) The procedure is carried out as described in Example 1(c) but with the use of 275 g (1.075 mols) of 2,2-dimethyl-11-ethyl-11-amino-undecanal-oxime. Distillation yields 215 g (0.887 mol) of 1-ethyl-10,10-dimethyl-1,11-diaminoundecane; yield 82.6% of theory.

EXAMPLE 5

(a) In a manner analogous to that described in Example 1(a) 495 g (3.41 mols) of N-benzylidene-propenylamine is reacted with 1,3-butadiene. The reaction mixture is distilled to yield 750 g (2.97 mols) of 3-methyl-12-phenyl-1-aza-1,5,9-cyclododecatriene as a cis-trans isomeric mixture (cis:trans=65:35); b.p. 112°–113° C./1 Pa; $n_D^{20} = 1.5505$; m.p. (cis isomer)=57°–58° C.

(b) 502 g (1.98 mols) of 3-methyl-12-phenyl-1-aza-1,5,9-cyclododecatriene is added to 220 g of 37% hydrochloric acid, in the course of 1.5 hours, in such a manner that the temperature does not exceed 80° C. The mixture is then cooled to room temperature (20°–25° C.), and 140 g (2.02 mols) of hydroxylamine hydrochloride is added. There is subsequently added during one hour, with water-bath cooling, about 185 g (4.6 mols) of solid sodium hydroxide until the pH of the aqueous solution is 10–11. The organic phase which precipitates is separated and washed neutral with water. The yield is 567 g (1.98 mols) of 2-methyl-11-phenyl-11-aminoundeca-4,8-dienal-oxime in the form of highly viscous liquid. MS spectrum: molecular peak 286, masses of the fragments 269, 254, 214, 148, 121, 106.

(c) The procedure is carried out as described in Example 1(c) but with the use of 567 g (1.98 mols) of 2-methyl-11-phenyl-11-amino-undeca-4,8-dienal-oxime. Distillation yields 441 g (1.6 mols) if 1-phenyl-10-methyl-1,11-diaminoundecane; yield 80.7% of theory; b.p. 138°–140° C./1 Pa; $n_D^{20} = 1.5095$.

Analysis for $C_{18}H_{32}N_2$ (molecular weight 276.47): calculated: C 78.20%, H 11.67%, N 10.13%, found: C 78.34%, H 11.83%, N 10.03%.

MS spectrum: molecular peak 276, masses of the fragments 230, 106, 79, 44.

$^1$H-NMR spectrum $\tau$(ppm): 272(s), 6.14(t), 7.45(m), 8.2–8.8(m), 9.08(d) in the ration of 5:1:2:21:3.

EXAMPLE 6

(a) 253 g (1 mol) of 3-methyl-12-phenyl-1-aza-1,5,9-cyclododecatriene is dissolved in 2 liters of cyclohexane, and the solution is hydrogenated at 20°–25° C. under an initial pressure of 100 bars, in the presence of 40 g of rhodium/aluminium oxide, for 4 hours in a steel autoclave. After distilling off the solvent, there is obtained as the main fraction 242 g (0.94 mol) of 3-methyl-12-phenyl-1-aza-cyclododecene as a cis-trans isomeric mixture; b.p. 112° C./4 Pa.

(b) The procedure is carried out as described in Example 1(b) but with the use of 146 g (0.568 mol) of 3-methyl-12-phenyl-1-aza-cyclododecene, 47 g (0.286 mol) of hydroxylamine sulfate, 60 g (0.61 mol) of sulfuric acid and 200 ml of water. The yield after processing as described in Example 1(b) is 165 g (0.567 mol) of 2-methyl-11-phenyl-11-aminoundecanal-oxime as highly viscous liquid.

(c) The procedure is carried out as described in Example 1(c) but with the use of 165 g (0.567 mol) of 2-methyl-11-phenyl-11-amino-undecanal-oxime. After distillation, there is obtained 110 g (0.399 mol) of 1-phenyl-10-methyl-1,11-diaminoundecane; yield 70.3% of theory.

EXAMPLE 7

(a) Analogously to the manner described in Example I(a), 110 g (1.13 mols) of N-isopropylidene-propenylamine [produced by reaction of acetone with allylamine, and subsequent isomerisation; Zhurnal Organicheskoi Khimii, 6, No. 11, 2197-9 (1970)] is reacted with 108 g (2 mols) of 1,3-butadiene. Distillation yields 187.0 g (0.91 mol) of 3,12,12-trimethyl-1-aza-1,5,9-cyclododecatriene; b.p. 55° C./4 Pa; $n_{20}^{20} = 1.4895$.

(b) The procedure is carried out in the manner described in Example 1(b) but with the use of 205 g (1 mol) of 3,12,12-trimethyl-1-aza-1,5,9-cyclododecatriene, 82 g (0.5 mol) of hydroxylamine sulfate, 110 g of sulfuric acid and 300 ml of water. After further processing and subsequent distillation, the yield is 205 g (0.86 mol) of 2,11,11-trimethyl-11-aminoundeca-4,8-dienal-oxime, b.p. 155° C./20 Pa; $n_D^{20} = 1.4950$.

(c) The procedure as described in Example 1(c) is carried out but with the use of 202 g (0.848 mol) of 2,11,11-trimethyl-11-amino-undeca-4,8-dienal-oxime. The yield after distillation is 173 g (0.758 mol) of 1,1,10-trimethyl-1,11-diaminoundecane; yield 89.4% of theory; b.p. 87° C./4 Pa; $n_D^{20} = 1.4585$.

Analysis for $C_{14}H_{32}N_2$ (molecular weight 228.42): calculated: C 73.62%, H 14.12%, N 12.27%, found: C 73.42%, H 14.20%, N 12.31%.

MS spectrum: molecular peak 228, masses of the fragments 213, 199, 182, 154, 126, 84, 70, 58. $^1$H-NMR spectrum $\tau$(ppm): 7.48(m), 8.68(s), 8.90(s), 9.09(d) in the ratio of 2:21:6:3.

EXAMPLE 8

(a) In a manner analogous to that described in Example 1(a), 273 g (2.02 mols) of N-2-furylidene-propenylamine [produced by reaction of 2-furylaldehyde with allylamine, and subsequent isomerisation in the presence of potassium tert-butylate; b.p. 60°–62° C./67 Pa; $n_D^{20} = 1.6004$] is reacted with 1,3-butadiene. The yield on distillation is 210 g (0.865 mol) of 3-methyl-12-(2-furyl)-1-aza-1,5,9-cyclododecatriene; b.p. 106°–108° C./4 Pa; $n_D^{20} = 1.5260$.

(b) The procedure as described in Example 1(b) is carried out but with the use of 190 g (0.78 mol) of 3-methyl-12-(2-furyl)-1-aza-1,5,9-cyclododecatriene, 54 g (0.78 mol) of hydroxylamine hydrochloride, 84 g of sulfuric acid, 300 ml of water and 65 g of solid sodium hydroxide. The organic phase which precipitates contains 201 g (0.728 mol) of 2-methyl-11-(2-furyl)-11-amino-undeca-4,8-dienal-oxime; $n_D^{20} = 1.5305$.

(c) The procedure as described in Example 1(c) is carried out but with the use of 276 g (1 mol) of 2-methyl-11-(2-furyl)-11-amino-undeca-4,8-dienal-oxime. The yield on distillation is 224 g (0.842 mol) of 1-(2-furyl)-10-methyl-1,11-diaminoundecane; yield 84.2% of theory; b.p. 135°–138° C./7 Pa; $n_D^{20} = 1.4869$.

Analysis for $C_{16}H_{30}N_2O$ (molecular weight 266.43): calculated: C 72.13%, H 11.35%, N 10.52%, O 6.01%, found: C 72.08%, H 11.38%, N 10.43%, O 6.25%.

MS spectrum: molecular peak 266, masses of the fragments 244, 220, 199, 96.

$^1$H-NMR spectrum $\tau$(ppm): 2.69(d), 3.72(dd), 3.93(d), 6.13(t), 7.46(m), 8.1–8.8(m), 9.08(d) in the ratio of 1:1:1:1:2:21:3.

EXAMPLE 9

(a) The procedure is carried out as described in the preceding Examples but with the use of 72.4 g (0.4 mol) of 1-(3-pentyl)-4,4-diethyl-2-aza-1,3-butadiene [produced by reaction of 2-ethylbutyraldehyde with ammonia according to the U.S. Patent Specification No. 2,319,848] and 48.4 g (0.895 mol) of 1,3-butadiene. The yield after processing is 56.8 g (0.197 mol) of 3,3-diethyl-12-(3-pentyl)-1-aza-1,5,9-cyclododecatriene; b.p. 90°–92° C./0.13 Pa; $n_D^{20} = 1.4840$.

(b) The procedure is carried out as described in Example 2(a) but with the use of 289 g (1 mol) of 3,3-diethyl-12-(3-pentyl)-1-aza-1,5,9-cyclododecatriene. There is obtained on distillation 265 g (0.905 mol) of 3,3-diethyl-12-(3-pentyl)-1-aza-cyclododecene; b.p. 95° C./4 Pa.

(c) The procedure is carried out as described in Example 2(b) but with the use of 320 g (1.09 mols) of 3,3-diethyl-12-(3-pentyl)-1-aza-cyclododecene, 89.5 g (0.546 mol) of hydroxylamine sulfate, 110 g of 37% hydrochloric acid and 400 ml of water. On neutralisation with solid sodium hydroxide, there is obtained 350 g (1.07 mols) of 2,2-diethyl-11-(3-pentyl)-11-amino-undecanal-oxime; $n_D^{20} = 1.4637$.

(d) The procedure is carried out as described in Example 1(c) but with the use of 243 g (0.745 mol) of 2,2-diethyl-11-(3-pentyl)-11-amino-undecanal-oxime. There is obtained on distillation 199 g (0.638 mol) of 1-(3-pentyl)-10,10-diethyl-1,11-diaminoundecane; yield 85.6% of theory; b.p. 133°–135° C./3 Pa; $n_D^{20}=1.4704$.

Analysis for $C_{20}H_{44}N_2$ (molecular weight 312.59): calculated: C 76.85%, H 14.19%, N 8.96%, found: C 77.05%, H 13.92%, N 8.94%.

MS spectrum: molecular peak 312, masses of the fragments 283, 241, 224, 212, 128, 100.

$^1$-H-NMR spectrum $\tau$(ppm): 7.2(m), 7.55(s), 8.2–8.9(m), 9.0–9.3(m) in the ratio of 1:2:25:16.

EXAMPLE 10

(a) In a manner analogous to that described in Example 1(a), 710 g (3.93 mols) of N-2-methyl-pentylidene-(2-methylpenten-1-yl-amine) [produced by reaction of 2-methylvaleraldehyde with ammonia according to U.S. Pat. No. 2,319,848] is reacted with 432 g (8.0 mols) of 1,3-butadiene. The yield after further processing the reaction mixture is 995 g (3.45 mols) of 3-methyl-3-n-propyl-12-(2-pentyl)-1-aza-1,5,9-cyclododecatriene as an isomeric mixture (2 main isomers); b.p. 103°–105° C./40 Pa; $n_D^{20}=1.4886$.

(b) The procedure as described in Example 2(a) is carried out but with the use of 289.5 g (1 mol) of 3-methyl-3-n-propyl-12-(2-pentyl)-1-aza-1,5,9-cyclododecatriene. There is obtained on distillation 263 g (0.896 mol) of 3-methyl-3-n-propyl-12-(2-pentyl)-1-aza-cyclododecene; b.p. 125° C./53 Pa.

(c) The procedure is carried out as described in Example 2(b) but with the use of 293.55 g (1 mol) of 3-methyl-3-n-propyl-12-(2-pentyl)-1-aza-cyclododecene, 82.1 g (0.5 mol) of hydroxylamine sulfate, 100 g of 37% hydrochloric acid, 400 ml of water and 85 g of solid sodium hydroxide. The organic phase precipitating contains 325 g (0.996 mol) of 2-methyl-2-n-propyl-11-(2-pentyl)-11-amino-undecanal-oxime; yield 99.6% of theory.

(d) The procedure is carried out as described in Example 1(c) but with the use of 325 g (0.996 mol) of 2-methyl-2-n-propyl-11-(2-pentyl)-11-amino-undecanal-oxime. Distillation yields 285 g (0.912 mol) of 1-(2-pentyl)-10-methyl-10-n-propyl-1,11-diaminoundecane; yield 91.5% of theory; b.p. 140°–142° C./3 Pa; $n_D^{20}=1.4665$.

Analysis for $C_{20}H_{44}N_2$ (molecular weight 312.59): calculated: C 76.85%, H 14.19%, N 8.96%, found: C 77.15%, H 14.52%, N 9.02%.

MS spectrum: molecular peak 312, masses of the fragments 283, 241, 224, 212, 100.

$^1$H-NMR spectrum $\tau$(ppm): 7.42(m), 7.56(s), 8.5–8.9(m), 9.05–9.24(m) in the ratio of 1:2:25:16.

EXAMPLE 11

(a) In a manner analogous to that described in Example 1(a), 760 g (3.21 mols) of N-2-ethyl-hexylidene-(2-ethylhexen-1-yl-amine) [produced by reaction of 2-ethylcapronaldehyde with ammonia according to U.S. Pat. No. 2,319,848] is reacted with 378 g (7 mols) of 1,3-butadiene. There is obtained on processing the reaction mixture 930 g (2.69 mols) of 3-ethyl-3-n-butyl-12-(3-heptyl)-1-aza-1,5,9-cyclododecatriene as a 7:3 isomeric mixture; b.p. 106°–109° C./13 Pa; $n_D^{20}=1.4895$.

(b) The procedure is carried out in the manner described in Example 2(a) but with the use of 396 g (1.15 mols) of 3-n-butyl-3-ethyl-12-(3-heptyl)-1-aza-1,5,9-cyclododecatriene. There is obtained on distillation 384 g (1.1 mols) of 3-n-butyl-3-ethyl-12-(3-heptyl)-1-aza-cyclododecene; b.p. 130° C./4 Pa.

(c) The procedure is carried out as described in Example 2(b) but with the use of 300 g (0.589 mol) of 3-n-butyl-3-ethyl-12-(3-heptyl)-1-aza-cyclododecene, 70.3 g (0.43 mol) of hydroxylamine sulfate and 85 g of 37% hydrochloric acid and 400 ml of water. The yield after neutralisation with solid sodium hydroxide is 329 g (0.86 mol) of 2-n-butyl-2-ethyl-11-(3-heptyl)-11-aminoundecanal-oxime; yield 100% of theory.

(d) The procedure is carried out as described in Example 1(c) but with the use of 248 g (0.648 mol) of 2-n-butyl-2-ethyl-11-(3-heptyl)-11-amino-undecanal-oxime. There is obtained on distillation 195 g (0.53 mol) of 1-(3-heptyl)-10-n-butyl-10-ethyl-1,11-diaminoundecane; yield 81.6% of theory; b.p. 156°–160° C./4 Pa; $n_D^{20}=1.4672$.

Analysis for $C_{24}H_{52}N_2$ (molecular weight 368.69): calculated: C 78.19%, H 14.22%, N 7.60%, found: C 78.60%, H 14.44%, N 7.47%.

MS spectrum: molecular peak 368, masses of the fragments 339, 269, 240, 196, 128.

$^1$H-NMR spectrum $\tau$(ppm): 7.39(m), 7.56(s), 8.5–8.9(m), 9.05(s) and 9.1–9.3(m) in the ratio of 1:2:33:16.

EXAMPLE 12

(a) In a manner analogous to that described in Example 1(a), 467 g (2.8 mols) of N-propylidene-(2-ethyl-hexen-1-yl-amine) is reacted with 324 g (mols) of 1,3-butadiene. After a reaction time of 4 hours at 40° C., the yield after further processing is 624 g (2.27 mols) of 3,12-diethyl-3-n-butyl-1-aza-1,5,9-cyclododecatriene as an isomeric mixture; b.p. 98°–100° C./40 Pa; $n_D^{20}=1.4905$.

The N-propylidene-(2-ethyl-hexen-1-yl-amine used in the above Example was produced in a manner analogous to that in which N-propylidene-(2-methyl-propenylamine) was produced, but with the use of 10 g of potassium tert-butylate, 800 g (4.79 mols) of (2-ethyl-hexylidene)-allylamine and 600 ml of tetrahydrofuran. After a reaction time of 2 hours at 35° C., the yield is 682 g (4.08 mols) of N-propylidene-(2-ethyl-hexen-1-yl-amine) as an isomeric mixture in the weight ratio of 55:45; b.p. 53°–56° C./133 Pa; $n_D^{20}=1.4698$.

(b) The procedure is carried out as described in Example 2(a) but with the use of 275.5 g (1 mol) of 3-n-butyl-3,12-diethyl-1-aza-1,5,9-cyclododecatriene. The yield after distillation is 245.5 g (0.878 mol) of 3-n-butyl-3,12-diethyl-1-aza-cyclododecene; b.p. 110° C./7 Pa.

(c) The procedure is carried out in the manner described in Example 2b but with the use of 245.5 g (0.878 mol) of 3-n-butyl-3,12-diethyl-1-aza-cyclododecene, 74 g (0.45 mol) of hydroxylamine sulfate, 100 g of 37% hydrochloric acid and 200 ml of water. The yield after neutralisation with solid sodium hydroxide is 255 g (0.815 mol) of 2-n-butyl-2,11-diethyl-11-amino-undecanal-oxime.

(d) The procedure is carried out as described in Example 1(c) but with the use of 219 g (0.7 mol) of 2-n-butyl-2,11-diethyl-11-amino-undecanal-oxime. The yield on distillation is 164 g (0.55 mol) of 1,10-diethyl-10-n-butyl-1,11-diaminoundecane; yield 78.5% of theory; b.p. 128°–130° C./5 Pa; $n_D^{20}=1.4630$.

Analysis for $C_{19}H_{42}N_2$ (molecular weight 298.56): calculated: C 76.44%, H 14.18%, N 9.38%, found: C 76.62%, H 13.93%, N 9.48%.

MS spectrum: molecular peak 298, masses of the fragments 269, 240, 226, 199.

$^1$H-NMR spectrum (ppm): 7.4(m), 7.57(s), 8.4–8.85(m), 8.93(s) and 8.95–9.3(m) in the ratio of 1:2:26:13.

EXAMPLE 13

(a) In a manner analogous to that described in Example 1(a), 678 g (3.31 mols) of N-cyclohexyl-methylidene-(cyclohexylidene-methylamine) [produced by reaction of cyclohexanealdehyde with ammonia; b.p. 83° C./4 Pa; $n_D^{20}=1.5260$] is reacted with 1,3-butadiene. The yield on distillation is 851 g (2.72 mols) of 3,3-pentamethylene-12-cyclohexyl-1-aza-1,5,9-cyclododecatriene; b.p. 140° C./3 Pa; $n_D^{20}=1.5191$.

(b) The procedure is carried out in the manner described in Example 2(a) but with the use of 750 g (2.4 mols) of 3,3-pentamethylene-12-cyclohexyl-1-aza-1,5,9-cyclododecatriene. There is obtained on distillation 733.9 g (2.32 mols) of 3,3-pentamethylene-12-cyclohexyl-1-azacyclododecene; b.p. 140°–142° C./3 Pa; $n_D^{20}=1.4982$.

(c) The procedure is carried out as described in Example 2(b) but with the use of 317 g (1 mol) of 3,3-pentamethylene-12-cyclohexyl-1-aza-cyclododecene, 70 g (1 mol) of hydroxylamine hydrochloride, 100 g of 37% hydrochloric acid, 300 ml of water and 100 g of solid sodium hydroxide. The organic phase which precipitates contains 340 g (0.97 mol) of 2,2-pentamethylene-11-cyclohexyl-11-amino-undecanal-oxime; yield 97% of theory.

(d) The procedure is carried out in the manner described in Example 1(c) but with the use of 340 g (0.97 mol) of 2,2-pentamethylene-11-cyclohexyl-11-aminoundecanal-oxime. There is obtained on distillation 252 g (0.75 mol) of 1-cyclohexyl-10,10-pentamethylene-1,11-diaminoundecane; yield 77.2% of theory; b.p. 166°–170° C./3 Pa; $n_D^{20}=1.4975$.

Analysis for $C_{22}H_{44}N_2$ (molecular weight 336.61): calculated: C 78.50%, H 13.18%, N 8.32%, found: C 78.76%, H 13.42%, N 8.17%.

MS spectrum: molecular peak 336, masses of the fragments 307, 290, 267, 253, 236, 224, 128, 112.

$^1$H-NMR spectrum $\tau$(ppm): 7.48(s) and 7.56(m), 8.1–8.9(m), 9.02(s) in the ratio of 3:37:4.

EXAMPLE 14

(a) In a manner analogous to that described in Example 1(a), 1010 g (6.35 mols) of N-benzylidene-(2-methylpropenylamine) [produced by reaction of benzaldehyde with methallylamine and subsequent isomerisation in the presence of potassium tert-butylate; b.p. 65°–66° C./7 Pa; $n_D^{20}=1.5836$] is reacted with 1,3-butadiene. After a reaction of 2 hours at 85° C. and subsequent distillation, the yield is 1398 g (5.24 mols) of 3,3-dimethyl-12-phenyl-1-aza-1,5,9-cyclododecatriene; b.p. 128°–130° C./4 Pa; b.p. 66°–68° C.

(b) The procedure as described in Example 1(b) is carried out but with the use of 289.3 g (1.09 mols) of 3,3-dimethyl-12-phenyl-1-aza-1,5,9-cyclododecatriene, 88.7 g (0.54 mol) of hydroxylamine sulfate, 100 g of 37% hydrochloric acid, 400 ml of water and 100 g of solid sodium hydroxide. The organic phase which precipitates contains 320 g (1.065 mols) of 2,2-dimethyl-11-phenyl-11-amino-undeca-4,8-dienaloxime; yield 97.9% of theory.

(c) The procedure is carried out as described in Example 1(c) but with the use of 320 g (1.065 mols) of 2,2-dimethyl-11-phenyl-11-amino-undeca-4,8-dienaloxime. The yield on distillation is 296 g (1.02 mols) of 1-phenyl-10,10-dimethyl-1,11-diaminoundecane; yield 95.8% of theory; b.p. 150° C./3 Pa; $n_D^{20}=1.5054$.

Analysis for $C_{19}H_{34}N_2$ (molecular weight 290.50): calculated: C 78.56%, H 11.80%, N 9.64%, found: C 76.61%, H 11.97%, N 9.76%.

MS spectrum: molecular peak 290, masses of the fragments 261, 244, 213, 188, 106, 91.

$^1$H-NMR spectrum $\tau$(ppm): 2.76(s), 6.13(t), 7.56(s), 8.3(m), 8.7(s) and 8.78(s), 9.13(s) in the ratio of 5:1:2:2:18:6.

EXAMPLE 15

(a) Analogously to Example 1(a), 629 g (3.55 mols) of N-cyclopentyl-methylidene-(cyclopentylidenemethylamine) [produced by reaction of cyclopentanealdehyde with ammonia, b.p. 125° C./1.86×10$^3$ Pa; $n_D^{20}=1.5245$] is reacted with 1,3-butadiene. The yield on distillation is 798 g (2.8 mols) of 3,3-tetramethylene-12-cyclopentyl-1-aza-1,5,9-cyclododecatriene; b.p. 120° C./1 Pa.

(b) The procedure is carried out in the manner described in Example 2(a) but with the use of 500 g (1.75 mols) of 3,3-tetramethylene-12-cyclopentyl-1-aza-1,5,9-cyclododecatriene. The yield on distillation is 470 g (1.63 mols) of 3,3-tetramethylene-12-cyclopentyl-1-azacyclododecene; b.p. 130° C./7 Pa.

(c) The procedure as described in Example 2(b) is carried out but with the use of 470 g (1.63 mols) of 3,3-tetramethylene-12-cyclopentyl-1-aza-cyclododecene, 133 g (0.81 mol) of hydroxylamine sulfate, 162 g of 37% hydrochloric acid and 400 ml of water. The yield after neutralisation with solid sodium hydroxide is 525 g (1.63 mols) of 2,2-tetramethylene-11-cyclopentyl-11-aminoundecanal-oxime; yield 100% of theory.

(d) The procedure is carried out in the manner described in Example 1(c) but with the use of 525 g (1.63 mols) of 2,2-tetramethylene-11-cyclopentyl-11-aminoundecanal-oxime. There is obtained on distillation 432 g (1.405 mols) of 1-cyclopentyl-10,10-tetramethylene-1,11-diaminoundecane; yield 86.1% of theory; b.p. 166°–168° C./5 Pa; $n_D^{20}=1.4922$.

Analysis for $C_{20}H_{40}N_2$ (molecular weight 308.55): calculated: C 77.85%, H 13.07%, N 9.08%, found: C 77.91%, H 13.37%, N 9.00%.

MS spectrum: molecular peak 308, masses of the fragments 290, 279, 262, 239, 222, 210, 98.

$^1$H-NMR spectrum $\tau$(ppm): 7.50(m), 8.1–8.8(m), 8.93(s) in the ratio of 3:33:4.

EXAMPLE 16

78.6 g (0.285 mol) of 1-phenyl-10-methyl-1,11-diaminoundecane produced according to Example 5, together with 400 ml of methanol and 8 g of a ruthenium/charcoal catalyst (10 percent by weight of ruthenium) are placed into a steel autoclave, and hydrogenated for 5 hours at 120° C. under a hydrogen pressure of 100 bars. There is obtained on processing the reaction mixture 42.7 g (0.152 mols) of 1-cyclohexyl-10-methyl-1,11-diaminoundecane; yield 53.3% of theory; b.p. 136°–138° C./4 Pa; $n_D^{20}=1.4809$.

Analysis for $C_{18}H_{38}N_2$ (molecular weight 282.52): calculated: C 76.53%, H 13.56%, N 9.92%, found: C 76.39%, H 13.38%, N 9.58%.

$^1$H-NMR spectrum $\tau$(ppm): 7.5(m), 8.1–8.7(m) and 8.84(s), 9.07(d) in the ratio of 3:32:3.

EXAMPLE 17

In the manner described in Example 16, 143 g (0.439 mol) of 1-phenyl-10,10-dimethyl-1,11-diaminoundecane is hydrogenated. There is obtained on distillation 95 g (0.321 mol) of 1-cyclohexyl-10,10-dimethyl-1,11-diaminoundecane; yield 65% of theory; b.p. 147° C./4 Pa; $n_D^{20}=1.4805$.

Analysis for $C_{19}H_{40}N_2$ (molecular weight 296.54): calculated: C 76.96%, H 13.60%, N 9.45%, found: C 77.08%, H 13.87%, N 9.32%.

MS spectrum: molecular peak 296, masses of the fragments 281, 267, 250, 227, 213, 196, 184, 128, 112.

$^1$H-NMR spectrum $\tau$(ppm): 7.5(m) and 7.59(s), 8.1–8.9(m), 9.02(s), 9.14(s) in the ratio of 3:27:4:6.

EXAMPLE 18

(a) The procedure is carried out as described in Example 1(a) but with the use of 302.5 g (2 mols) of N-cyclohexylidene-(2-methylpropenylamine) and 250 g (4.62 mols) of 1,3-butadiene. Distillation yields 382 g (1.48 mols) of 3,3-dimethyl-12,12-pentamethylene-1-aza-1,5,9-cyclododecatriene; b.p. 96° C./4 Pa; $n_D^{20}=1.5116$. The N-cyclohexylidene-(2-methylpropenylamine) was produced from cyclohexanone and methallylamine, and subsequent isomerisation of the reaction product with potassium tertbutylate; b.p. 96° C./1700 Pa; $n_D^{20}=1.5160$.

(b) The procedure is performed as described in Example 1(b) but with the use of 259.5 g (1 mol) of 3,3-dimethyl-12,12-pentamethylene-1-aza-1,5,9-cyclododecatriene, 69.5 g (1 mol) of hydroxylamine hydrochloride, 20 g of 37% hydrochloric acid and 250 ml of water. The yield on processing is 219.3 g of 2,2-dimethyl-11,11-pentamethylene-11-amino-undeca-4,8-dienal-oxime; yield 74.5% of theory; $n_D^{20}=1.5117$.

(c) The procedure is carried out as described in Example 1(c) but with the use of 160 g (0.545 mol) of 2,2-dimethyl-11,11-pentamethylene-11-amino-undeca-4,8-dienal-oxime. The yield on distillation is 127 g (0.45 mol) of 1,1-pentamethylene-10,10-diethyl-1,11-diaminoundecane; yield 82.5% of theory; b.p. 112° C./4 Pa; $n_D^{20}=1.4833$.

Analysis for $C_{18}H_{38}N_2$ (molecular weight 282.52): calculated: C 76.53%, H 13.56%, N 9.92%, found: C 76.71%, H 13.33%, N 9.81%.

MS spectrum: molecular peak 282, masses of the fragments 253, 239, 208, 180, 126, 98.

$^1$H-NMR spectrum $\tau$(ppm): 7.58(s), 8.4–8.8(m), 8.94(s), 9.13(s) in the ratio of 2:26:4:6.

EXAMPLE 19

(a) The procedure is carried out as described in Example 1(a) but with the use of 94.2 g (0.564 mol) of N-heptylidene(2-methylpropenylamine) [1-n-hexyl-4,4-dimethyl-2-aza-1,3-butadiene] and 80 g (1.48 mols) of 1,3-butadiene. The yield on distillation is 113 g (0.41 mol) of 3,3-dimethyl-12-n-hexyl-1-aza-1,5,9-cyclododecatriene; b.p. 100° C./4 Pa; $n_D^{20}=1.4841$.

The N-heptylidene-(2-methylpropenylamine) was produced from heptanal and methallylamine, with subsequent isomerisation of the reaction product with potassium tertbutylate; b.p. 54° C./5 Pa; $n_D^{20}=1.4662$.

(b) The procedure is carried out in the manner described in Example 1(b) but with the use of 113 g (0.41 mol) of 3,3-dimethyl-12-hexyl-1-aza-1,5,9-cyclododecatriene, 33 g (0.202 mol) of hydroxylamine sulfate, 50 g of concentrated hydrochloric acid and 250 ml of water. There is obtained after processing 125 g (0.405 mol) of 2,2-dimethyl-11-n-hexyl-11-amino-undeca-4,8-dienal-oxime; yield 99% of theory.

(c) The procedure is carried out as described in Example 1(c) but with the use of 116 g (0.377 mol) of 2,2-dimethyl-11-n-hexyl-11-amino-undeca-4,8-dienal-oxime. There is obtained on distillation 78 g (0.262 mol) of 1-n-hexyl-10,10-dimethyl-1,11-diaminoundecane; yield 69.5% of theory; b.p. 135° C./4 Pa; $n_D^{20}=1.4624$.

Analysis for $C_{19}H_{42}N_2$ (molecular weight 298.56): calculated: C 76.44%, H 14.18%, N 9.38%, found: C 76.61%, H 14.02%, N 9.22%.

MS spectrum: molecular peak 298, masses of the fragments 283, 269, 213, 196, 184, 128, 114.

$^1$H-NMR spectrum (ppm): 7.35(m), 7.57(s), 8.5–8.8(m), 8.92(s), 9.13(m) in the ratio of 1:2:26:4:9.

EXAMPLE 20

(a) The procedure is carried out as described in Example 1(a) but with the use of 222.4 g (2.0 mols) of N-isopropylidene-(2-methylpropenylamine). There is obtained by distillation 300 g (1.37 mols) of 3,3,12,12-tetramethyl-1-aza-1,5,9-cyclododecatriene; b.p. 58° C./4 Pa; $n_D^{20}=1.4858$. The N-isopropylidene-(2-methylpropenylamine) was produced from acetone and methallylamine, and by subsequent isomerisation of the reaction product; b.p. 89°–90° C.; $n_D^{20}=1.4762$.

(b) The procedure is carried out in the manner described in Example 1(b) but with the use of 110 g (0.5 mol) of 3,3,12,12-tetramethyl-1-aza-1,5,9-cyclododecatriene, 41 g (0.25 mol) of hydroxylamine sulfate, 50 ml of concentrated hydrochloric acid and 250 ml of water. There is obtained on distillation 85 g (0.337 mol) of 2,2,11,11-tetramethyl-11-amino-undeca-4,8-dienal-oxime; yield 67.4% of theory; b.p. 130° C./7 Pa.

(c) The procedure is carried out in the manner described in Example 1c but with the use of 126 g (0.5 mol) of 2,2,11,11-tetramethyl-11-amino-undeca-4,8-dienal-oxime. There is obtained by distillation 91 g (0.377 mol) of 1,1,10,10-tetramethyl-1,11-diaminoundecane; yield 75.3% of theory; b.p. 92° C./5 Pa; $n_D^{20}=1.4590$.

Analysis for $C_{15}H_{34}N_2$ (molecular weight 242.45): calculated: C 74.31%, H 14.14%, N 11.56%, found: C 74.47%, H 14.15%, N 11.57%.

MS spectrum: molecular peak 242, masses of the fragments 227, 210, 196, 140, 97.

$^1$H-NHR spectrum $\tau$(ppm): 7.58(s), 8.6–8.8(m), 8.88 and 8.89(s), 9.12(s) in the ratio of 2:16:10:6.

EXAMPLE 21

(a) The procedure is carried out as described in Example 1(a) but with the use of 93.6 g (0.5 mol) of N-benzylidene(2-ethyl-1-butenylamine) [1-phenyl-4,4-diethyl-2-aza-1,3-butadiene, produced from benzylamine and 2-ethyl-butenyl with subsequent isomerisation of the reaction product in the presence of potassium tert-butylate; b.p. 70° C./7 Pa; $n_D^{20}=1.5598$; see J. Org. Chem., 43, No. 4, 782–84 (1978)]. Distillation yields 116 g (0.393 mol) of 3,3-diethyl-12-phenyl-1-aza-1,5,9-cyclododecatriene; b.p. 105° C./4 Pa; $n_D^{20}=1.5369$.

(b) The procedure is carried out in the manner described in Example 1(b) but with the use of 95.3 g (0.323 mol) of 3,3-diethyl-12-phenyl-1-aza-1,5,9-cyclododecatriene, 20 g of 37% hydrochloric acid, 22.4 g (0.322 mol) of hydroxylamine hydrochloride and 250 ml of water. The yield after processing is 103.1 g (0.314 mol) of 2,2-diethyl-11-phenyl-11-amino-undeca-4,8-dienal-oxime; yield 97.5% of theory.

(c) The procedure is carried out as described in Example 1(c) but with the use of 103 g (0.314 mol) of 2,2-diethyl-11-phenyl-11-amino-undeca-4,8-dienaloxime. The yield after distillation is 76 g (0.239 mol) of 1-phenyl-10,10-diethyl-1,11-diaminoundecane; yield 76% of theory; b.p. 146° C./2 Pa; $n_D^{20}=1.5090$.

Analysis for $C_{21}H_{38}N_2$ (molecular weight 318.55): calculated: C 79.18%, H 12.03%, N 8.79%, found: C 79.45%, H 12.08%, N 8.77%.

MS spectrum: molecular peak 318, masses of the fragments 289, 272, 213, 188, 131, 117, 106, 91.

$^1$H-NMR spectrum $\tau$(ppm): 2.72(s), 6.16(t), 7.58(s), 8.35(m), 8.6–8.9(m), 9.21(t) in the ratio of 5:1:2:2:22:6.

EXAMPLE 22

(a) The procedure is performed in the manner described in Example 1(a), but with the use of 215.3 g (1 mol) of N-benzylidene-(2-ethyl-1-hexenylamine) [1-phenyl-4-ethyl-4-n-butyl-2-aza-1,3-butadiene; produced by reaction of benzylamine with 2-ethyl-hexenal and subsequent isomerisation of the reaction product with potassium tert-butylate; b.p. 90° C./7 Pa; $n_D^{20}=1.5630$]. Distillation yields 288 g (0.891 mol) of 3-n-butyl-3-ethyl-12-phenyl-1-aza-1,5,9-cyclododecatriene; b.p. 130° C./2 Pa; $n_D^{20}=1.5296$.

(b) The procedure is carried out as described in Example 1(b) but with the use of 283.4 g (0.875 mol) of 3-n-butyl-3-ethyl-12-phenyl-1-aza-1,5,9-cyclododecatriene, 60.8 g (0.87 mol) of hydroxylamine hydrochloride, 50 ml of conc. hydrochloric acid and 250 ml of water. There is obtained after processing 310 g (0.87 mol) of 2-n-butyl-2-ethyl-11-phenyl-11-aminoundeca-4,8-dienal-oxime; yield 99.5% of theory.

(c) The process is carried out in the manner described in Example 1(c) but with the use of 310 g (0.87 mol) of 2-n-butyl-2-ethyl-11-phenyl-11-amino-undeca-4,8-dienaloxime. The yield on distillation is 205 g (0.593 mol) of 1-phenyl-10-n-butyl-10-ethyl-1,11-diaminoundecane; yield 68.1% of theory; b.p. 155°–158° C./5 Pa; $n_D^{20}=1.5045$.

Analysis for $C_{23}H_{42}N_2$ (molecular weight 346.60): calculated: C 79.70%, H 12.21%, N 8.08%, found: C 79.48%, H 12.46%, N 8.29%.

MS spectrum: molecular peak 346, masses of the fragments 317, 300, 188, 106, 91.

$^1$H-NMR spectrum $\tau$(ppm): 2.73(s), 6.18(t), 7.58(s), 8.35(m), 8.6–8.9(m), 9.08() and 9.22(t) in the ratio of 5:1:2:2:26:6.

EXAMPLE 23

(a) The procedure is carried out as described in Example 1(a) but with the use of 184 g (1.34 mols) of N-(2-ethyl)-buten-2-ylidene-propenylamine [produced by reaction of 2-ethyl-butenal and allylamine, and subsequent isomerisation of the reaction product, analogously to Zhurnal Organicheskoi Khimii, 6, No. 11, 2197-9 (1970); b.p. 70° C./1700 Pa; $n_D^{20}=1.5227$]. There is obtained on distillation 295 g (1.21 mols) of 3-methyl-12-(3-penten-2-yl)-1-aza-1,5,9-cyclododecatriene; b.p. 100° C./4 Pa; $n_D^{20}=1.5056$.

(b) The procedure is carried out in the manner described in Example 1(b) but with the use of 122.7 g (0.5 mol) of 3-methyl-12-(3-penten-2-yl)-1-aza-1,5,9-cyclododecatriene, 41.1 g (0.25 mol) of hydroxylamine sulfate, 50 ml of concentrated hydrochloric acid and 250 ml of water. There is obtained on further processing 135.9 g (0.488 mol) of 2-methyl-11-(3-penten-2-yl)-11-amino-undeca-4,8-dienal-oxime; yield 97.6% of theory; $n_D^{20}=1.5091$.

(c) The procedure is carried out as described in Example 1(c) but with the use of 135 g (0.485 mol) of 2-methyl-11-(3-penten-2-yl)-11-amino-undeca-4,8-dienal-oxime. The yield on distillation is 95 g (0.352 mol) of 1-(3-pentyl)-10-methyl-1,11-diaminoundecane; yield 72.5% of theory; b.p. 115° C./5 Pa; $n_D^{20}=1.4662$.

Analysis for $C_{17}H_{38}N_2$ (molecular weight 270.51): calculated: C 75.48%, H 14.16%, N 10.36%, found: C 75.50%, H 14.11%, N 10.41%.

MS spectrum: molecular peak 270, masses of the fragments 241, 199, 182, 170, 100.

$^1$H-NMR spectrum $\tau$(ppm): 7.2–7.6(m), 7.68(s), 7.85(s), 9.1(m) in the ratio of 3:22:4:9.

EXAMPLE 24

(a) The procedure is carried out as described in Example 1(a) but with the use of 105 g (0.765 mol) of N-(2-ethyl)-buten-2-ylidene-propenylamine and 120 g (1.76 mols) of isoprene. After a reaction time of 5 hours at 90° C., there is obtained on subsequent distillation 85 g (0.312 mol) of 3,5(or 6),9(or 10)-trimethyl-12-(3-penten-2-yl)-1-aza-1,5,9-cyclododecatriene; b.p. 108°–110° C./5 Pa; $n_D^{20}=1.5078$.

(b) The procedure is carried out in the manner described in Example 1(b) but with the use of 83.75 g (0.305 mol) of the above 1-aza-1,5,9-cyclododecatriene, 26.8 g (0.163 mol) of hydroxylamine sulfate, 35 ml of concentrated hydrochloric acid and 250 ml of water. The yield after processing is 90 g (0.294 mol) of 2,4(5),8(9)-trimethyl-11-(3-penten-2-yl)-11-amino-undeca-4,8-dienal-oxime; yield 96.5% of theory.

(c) The procedure is carried out in the manner described in Example 1(c) but with the use of 35 g (0.117 mol) of 2,4(5),8(9)-trimethyl-11-(3-penten-2-yl)-11-amino-undeca-4,8-dienal-oxime. The yield after distillation is 33.5 g (0.112 mol) of 1-(3-pentyl)-3(4),7(8),10-trimethyl-1,11-diaminoundecane; yield 95.5% of theory; m.p. 117° C./2 Pa; $n_D^{20}=1.4731$.

Analysis for $C_{19}H_{42}N_2$ (molecular weight 298.56): calculated: C 76.44%, H 14.18%, N 9.38%, found: C 76.5%, H 14.0%, N 9.2%.

MS spectrum: no molecular peak, masses of the fragments 269, 227, 210, 198, 100.

$^1$H-NMR spectrum $\tau$(ppm): 7.0–7.65(m), 8.2–8.95(m), 8.95–9.2(m) in the ratio of 3:24:15.

EXAMPLE 25

(a) The procedure as described in Example 1(b) is followed but with the use of 23.3 g (0.1 mol) of 3,3-dimethyl-12-isopropyl-1-aza-1,5,9-cyclododecatriene, 20 g of 37% hydrochloric acid, 20 ml of water and 10.8 g (0.1 mol) of phenylhydrazine. On processing as described in Example 1(b), there is obtained 34.1 g (0.1 mol) of 2,2-dimethyl-11-isopropyl-11-amino-undeca-4,8-dienal-phenylhydrazone; yield 100% of theory.

Analysis for $C_{22}H_{35}N_3$ (molecular weight 341.54): calculated: C 77.37%, H 10.33%, N 12.30%, found: C 77.03%, H 10.58%, N 12.23%.

MS spectrum: molecular peak 341, masses of the fragments 298, 270, 234, 161, 92, 72.

$^1$H-NMR spectrum $\tau$(ppm): 2.65–3.3(m), 4.56(m), 7.45(dt), 7.87(m), 8.03(s), 8.35(m), 8.88(s), 9.06(dd) in the ratio of 7:4:1:8:1:6:6.

(b) The procedure is carried out in the manner described in Example 1(c) but with the use of 34.1 g (0.1 mol) of 2,2-dimethyl-11-isopropyl-11-amino-undeca-4,8-dienal-phenylhydrazone. After a reaction time of 15 hours at 100° C. under a hydrogen pressure of 100 bars and subsequent processing, there is obtained 19.5 g (0.076 mol) of 1-isopropyl-10,10-dimethyl-1,11-diaminoundecane; yield 76% of theory.

EXAMPLE 26

(a) The procedure as described in Example 1(b) is followed but with the use of 46.6 g (0.2 mol) of 3,3-dimethyl-12-isopropyl-1-aza-1,5,9-cyclododecatriene, 40 g of 37% hydrochloric acid, 40 ml of water and 5 g (0.1 mol) of hydrazine hydrate. The yield after processing is 42 g (0.84 ml) of di-(2,2-dimethyl-11-isopropyl-11-aminoundeca-4,8-dienal)-hydrazone; yield 84% of theory.

Analysis for $C_{32}H_{58}N_4$ (molecular weight 498.84): calculated: C 77.05%, H 11.72%, N 11.23%, found: C 77.83%, H 12.08%, N 10.84%.

MS spectrum: molecular peak 498, masses of the fragments 483, 455, 438, 426, 372, 318, 276.

$^1$H-NMR spectrum $\tau$(ppm): 2.38(s), 4.58(m), 7.5(m), 7.88(m), 8.1–8.7(m), 8.88(s), 9.06(dd) in the ratio of 2:8:2:16:6:12:12.

(b) The procedure is carried out in the manner described in Example 1(c) but with the use of 42 g (0.084 mol) of di-(2,2-dimethyl-11-isopropyl-11-amino-undeca-4,8-dienal)-hydrazine. The yield on distillation is 26 g (0.102 mol) of 1-isopropyl-10,10-dimethyl-diaminoundecane; yield 60.6% of theory.

EXAMPLE 27

(a) The procedure is carried out in the manner described in Example 1(b) but with the use of 23.3 g (0.1 mol) of 3,3-dimethyl-12-isopropyl-1-aza-1,5,9-cyclododecatriene, 20 g of 37% hydrochloric acid, 20 ml of water and 11.15 g (0.1 mol) of semicarbazide hydrochloride. The yield after processing is 26.5 g (0.086 mol) of 2,2-dimethyl-11-isopropyl-11-aminoundeca-4,8-dienal-semicarbazone; yield 86% of theory.

Analysis for $C_{17}H_{32}H_4O$ (molecular weight 308.47): calculated: C 66.19%, H 10.46%, N 18.16%, O 5.19%, found: C 68.5%, H 10.5%, N 17.4%, O 5.0%.

MS spectrum: molecular peak 308, masses of the fragments 265, 248, 205, 182, 129, 72.

$^1$H-NMR spectrum $\tau$(ppm): 0.9(m), 2.98(s), 4.32(s) 4.58(m), 7.48(dt), 7.9(m), 8.1–8.8(m), 8.91(s), 9.06(dd) in the ratio of 1:1:2:4:1:8:3:6:6.

(b) The procedure is carried out as described in Example 1(c) but with the use of 26.5 g (0.086 mol) of 2,2-dimethyl-11-isopropyl-11-amino-undeca-4,8-dienal-semicarbazone. The yield on distillation is 13.8 g (0.54 mol) of 1-isopropyl-10,10-dimethyl-1,11-diaminoundecane; yield 62.6% of theory.

EXAMPLE 28

(a) The procedure as described in Example 2(b) is followed but with the use of 68.5 g (0.5 mol) of 3,3-dimethyl-12-isopropyl-1-aza-cyclododecene, 50 g of 37% hydrochloric acid, 54 g (0.5 mol) of benzylamine and 200 ml of water. There is obtained after neutralisation with 22 g (0.55 mol) of solid sodium hydroxide 97 g (0.282 mol) of 2,2-dimethyl-11-isopropyl-11-amino-undecanal-benzylamine; yield 56.4% of theory.

Analysis for $C_{23}H_{40}N_2$ (molecular weight 344.59): calculated: C 80.17%, H 11.70%, N 8.13%, found: C 80.0%, H 12.1%, N 7.7%.

MS spectrum: molecular peak 344, masses of the fragments 301, 253, 161, 91.

$^1$H-NMR spectrum $\tau$(ppm): 2.7(m), 6.18(s), 7.3–9.2(m) in the ratio of 6:2:32.

(b) The procedure is carried out in the manner described in Example 1(c) but with the use of 97 g (0.282 mol) of 2,2-dimethyl-11-isopropyl-11-amino-undecanal-benzylamine and a platinum catalyst. Hydrogenation is performed for 10 hours at 100° C. under a hydrogen pressure of 100 bars. The yield after processing is 52 g (0.203 mol) of 1-isopropyl-10,10-dimethyl-1,11-diaminoundecane; yield 72% of theory.

EXAMPLE 29

116.7 g (0.5 mol) of 3,3-dimethyl-12-isopropyl-1-aza-1,5,9-cyclododecatriene is added dropwise, in the course of 20 minutes, to a mixture of 250 ml of isopropanol, 30 ml of water and 55 g (0.56 mol) of sulfuric acid. The mixture is refluxed for one hour, and is then fed, under a hydrogen pressure of 150 bars and at a temperature of 120° C., into an autoclave filled with 200 g of liquid ammonia and 500 ml of methanol. After a reaction time of 15 hours, the mixture is cooled, and the excess ammonia and hydrogen are released. On subsequent distillation under high vacuum, the yield is 93 g (0.364 mol) of 1-isopropyl-10,10-dimethyl-1,11-diaminoundecane; yield 72.5% of theory.

APPLICATION EXAMPLES

(A) PRODUCTION OF POLYAMIDES

EXAMPLE I

In a flask provided with stirrer, dropping funnel and reflux condenser, 54.5 g of terephthalic acid is suspended in a mixture of 750 ml of ethanol and 750 ml of water; the suspension is heated to reflux temperature, and there is then added from the dropping funnel 103.2 g of 1-(3-pentyl)-10,10-diethyl-1,11-diaminoundecane. After 20 minutes, the mixture is cooled to room temperature (20°–25° C.), and the salt which has precipitated is filtered off. The yield on drying in vacuo is 147 g of salt (93% of theory). 10 g of this salt is sealed under nitrogen into a bomb tube, and heated for one hour in a salt bath at 270° C., in the course of which the salt melts to form a colourless melt. After cooling to room temperature, the solidified melt is removed from the bomb tube, and is held in an open polycondensation apparatus, with the exclusion of air and the continuous passing through of nitrogen, for 6 hours at 270° C. On cooling, the viscous melt solidifies to form a transparent colourless substance. The reduced solution viscosity of the polyamide obtained, measured on a 0.5% solution in m-cresol at 25° C., is 0.91 dl/g; glass transition temperature, determined in a differential calorimeter (DSC), is 123° C.

A sheet, produced at 270° C. by means of a hydraulic press, is exposed at room temperature to a relative humidity of 65% until no further loss of weight can be detected. The saturation value is 0.7 percent by weight. When the sheet is exposed to the action of boiling water, no impairment of the transparency is detectable even after 6 hours.

EXAMPLE II

In a round-bottomed flask provided with stirrer, reflux condenser and dropping funnel, 0.1 mol of terephthalic acid in 300 ml of 70% ethanol is heated to boiling. From the dropping funnel there is then added to the boiling suspension, in the course of about 10 minutes, 0.1 mol of 1-cyclohexyl-10,10-pentamethylene-1,11-diaminoundecane, and any diamine residues adhering to the funnel are quantitatively flushed with some ethanol into the reaction mixture. The clear solution formed is allowed to cool with continuous stirring; the salt which has precipitated is filtered off, and dried at 90° C. in vacuo.

Into a bomb tube, provided with a screw cover and an excess pressure valve, are weighed the following components:

2.156 g of 4,4'-diamino-3,3'-dimethyldicyclohexylmethane, 1.502 g of isophthalic acid, 8.535 g of salt from 1-cyclohexyl-10,10-pentamethylene-1,11-diaminoundecane and terephthalic acid.

After the air in the bomb tube has been completely expelled by nitrogen, the bomb tube is sealed and is immersed in a salt bath, the temperature of which is 270° C. A homogeneous transparent melt has formed after 30–60 minutes. After an overall time of 3 hours, the pre-condensation is interrupted by removing the bomb tube from the salt bath and releasing the excess pressure by opening the valve. The solidified transparent precondensate is taken from the bomb tube and transferred to a condensation vessel. With the strict exclusion of air and the continuous passing through of nitrogen, the melt is polycondensed for 5 hours at a salt-bath temperature of 5 hours, whilst the reaction water is being continuously removed by the stream of nitrogen. The melt on cooling solidifies to form a transparent substance.

2–3 g each time of the copolyamide produced is moulded, in a heatable hydraulic press at 270° C., into a sheet having a thickness of about 0.4 mm to 1 mm. In order to determine the water absorption, the sheet is exposed at room temperature to a relative humidity of 65% until no further increase in weight can be detected. The saturation value is 1.2 percent by weight. The reduced solution viscosity of the copolyamide, measured on a 0.5% solution in m-cresol at 25° C., is 1.09 dl/g; glass transition temperature, determined in a differential calorimeter (DSC), is 166° C. The resistance of the transparency to boiling water is very good, that is to say, no impairment of the transparency of the copolyamide is detectable even after several days.

(B) USE AS CURING AGENT FOR EPOXIDE RESINS

EXAMPLES III TO XIV

As curing agents for epoxide resins, there are used the amines produced according to Examples 1, 2, 5, 6, 7, 14, 21 and 22 and, as a comparison, trimethylhexamethylenediamine.

The diamines according to the invention are characterised by having negligible intrinsic colour and a low viscosity. The proportion of curing agent, increased by virtue of the higher molecular weight, together with the low viscosity of the amines, results in a favourable viscosity of the mixture obtained together with the epoxide resin.

A surprising advantage of the novel amines is the extraordinarily favourable behaviour when standing open in air, as can be seen from the test results in the following Table.

TABLE I

| Curing agent produced according to Example | 1 and 2 | 7 | 5 and 6 | 14 | 21 | 22 | Trimethylhexamethylenediamine |
|---|---|---|---|---|---|---|---|
| viscosity 25° C. (mPa s) | 15 | <10 | 30 | 50 | 75 | 105 | <10 |
| soluble in $H_2O$ (yes or no) | NO | yes, cloudy | yes, warm | NO | NO | NO | yes |
| in methylethylketone | yes | yes | yes | yes | yes | yes | yes |
| in ethanol | yes | yes | yes | yes | yes | yes | yes |
| increase in weight after 24 h at room temperature (~5 g left standing open in can lid) | 6.1% | | 8% | 4.6% | 4.1% | 3.2% | 30% became viscous |

As reactant for the novel amines, there is used, as a typical epoxide resin, a liquid unmodified bisphenol-A epoxide resin (resin A) having a viscosity at 25° C. of 10,000 cP and an epoxide content of 5.35 equivalents/kg.

The resin is in each case carefully mixed in the stoichiometric proportion at 25° C. with the amine to be tested. A small part of the mixture is immediately taken for determination of the pot life at 40° C., which is defined as being the time taken for the viscosity of the mixture to increase to 3000 cP.

The main part of the mixture is subsequently carefully freed in vacuo from the air stirred in during mixing, and is then used as follows:

(a) Production of moulded plates for preparing test specimens. Moulded plates for producing test specimens are obtained by pouring the mixture into metal moulds of the following dimensions, with subsequent curing under the conditions given in Table 2:

aluminium moulds for producing plates 135×135×4 mm in size; from the moulding-material plates obtained by means of these moulds, there are sawn test specimens having dimensions 60×10×4 mm; these are used for determining flexural strength and deflection according to VSM Standard 77 103; impact bend strength according to VSM Standard 77 105; and the increase in weight after storage in water;

aluminium mould for producing test specimens having dimensions 120×10×4 mm for determining dimensional stability under heat (heat distortion according to Iso R 75); the glass transition temperature is determined thermoanalytically on a small specimen.

(b) Production of specimens for determining the tensile shearing strength: onto the ends of test strips from Anticorodal B, which have been roughened by grinding and cleaned by washing with acetone, and which have dimensions 170×25×1.5 mm, is applied a resin/curing agent mixture. Each pair of these test strips is so arranged with the aid of a gauge that the ends coated with the resin/curing agent mixture overlap by 10 mm. The specimens are then secured in this position by means of a tube clamp, and are subsequently cured under the conditions given in the Table.

(c) Production of test specimens for the tests relating to lacquering techniques. Iron plates, degreased by being washed with trichloroethylene and having dimensions 350×70×0.8 mm, are coated, by means of a bar coater, with a 50μ thick film of the respective resin/curing agent mixture. After curing under the conditions given in Table 3, the lacquered metal strips are used to determine the Erichsen cupping value, the impact cupping value and mandrel test value, and also the chemical resistance of the lacquer films. The procedure for this comprises in each case applying one drop of the test liquid concerned to the film, covering the spot with a watch glass, and finally assessing the appearance of the film after an action time of one hour at 23° C.

The compositions of the mixtures according to Examples III to VIII, the values of the pot life test, and a part of the test values obtained using the cured epoxide resin mixtures are summarised in Table 2. Further test values for lacquer systems follow in Table 3 (Examples IX to XIV).

The results summarised in Tables 2 and 3 verify that the novel amines are very suitable as curing agents for epoxide resins. It is worthy of note that, notwithstanding the clearly extended pot life, a curing of moulding materials and also of thin films at room temperature remains possible. Fully cured moulding materials and films are distinguished by good mechanical properties, with the high impact strength of the moulding materials being remarkable.

TABLE 2

| Example | III | | IV | | V | | VI | | VII | | VIII | | Comparative Example 1 | |
|---|---|---|---|---|---|---|---|---|---|---|---|---|---|---|
| curing agent, produced according to Example | 1 and 2 | | 7 | | 5 and 6 | | 14 | | 21 | | 22 | | THMD | |
| wt. % of curing agent relative to the epoxide resin | 34.6 | | 30.8 | | 37.3 | | 39.2 | | 42.9 | | 46.7 | | 21.3 | |
| pot life at 40° C. | 139 min. | | 114 min. | | 85 min. | | 111 min. | | | | | | 37 min. | |
| curing | A | B | A | B | A | B | A | B | A | B | A | B | A | B |
| A 1 week 25° B 24h 40° + 6h 100° C. | | | | | | | | | | | | | | |
| impact bend strength (KJ/m$^2$) | 14 | 56 | 12.5 | 73 | 8.3 | 53 | 40 | | | | | | 7.2 | 15.8 |
| flexural strength* (N/mm$^2$) | 88/43 | 86/65 | 77 | 80/51 | 76 | 90/58 | 102/74 | | | | | | 88 | 93 |
| deflection* (mm) | 5.5/17 | 8.0/18.5 | 3.8 | 8/18 | 3.9 | 7.5/19 | 8.0/15.5 | | | | | | 3.7 | 14.5 |
| heat distortion (°C.) | 60 | 90 | 63 | 97 | 57 | 85 | 96 | | | | | | 67 | 113 |
| GTT on TA2000 (°C.) | 61 | 95 | 57 | 109 | 57 | 98 | 108 | | 51 | 93 | 50 | 92 | 61 | 118 |
| H$_2$O absorption after 4 days at RT (%) | 0.18 | 0.26 | 0.23 | 0.22 | 0.25 | 0.22 | 0.11 | | | | | | 0.20 | 0.18 |
| H$_2$O absorption after 1 h in c.w.** | 0.47 | 0.33 | 0.47 | 0.30 | 0.45 | 0.29 | 0.33 | | | | | | 0.39 | 0.30 |
| tensile shearing strength (N/mm$^2$) | 8.9 | 14.1 | 8.2 | 15.1 | 7.9 | 13.3 | 20.2 | | | | | | 6.9 | 9.1 |

*when two values, 1. at max. load, 2. at fracture
**c.w. = cold water

TABLE 3

| Example | IX | X | XI | XII | XIII | XIV | Comparative Example 1 |
|---|---|---|---|---|---|---|---|
| curing agent produced according to Example | 1 and 2 | 7 | 5 and 6 | 14 | 21 | 22 | THMD |
| wt. % of curing agent relative to the epoxide resin | 34.6 | 30.8 | 37.3 | 39.2 | 42.9 | 46.7 | 21.3 |
| curing | | | | in each case 1 week at room temperature | | | |
| appearance of the lacquer film | o.k. high gloss | colourless, dull, rough | o.k. colourless | o.k. high gloss | o.k. high gloss | o.k. high gloss | slightly tacky surface |
| Erichsen cupping (mm) | 6.8 | 6.7 | 8 | 3.4 | 3.6 | 3.6 | 2.3 |
| impact test (cm/kg hammer) | 30/1 | 40/1 | 30/1 | <10/1 | <10/1 | <10.1 | <10.1 |
| mandrel ( ') | 180 | 180 | 30 | 75 | 100 | 90 | 70 |
| chemical resistance* | | | | | | | |
| 5n H$_2$SO$_4$ | 1 | 1 | 1 | 1 | 1 | 1 | 1 |
| 5n NaOH | 1 | 1 | 1 | 1 | 1 | 1 | 1 |
| H$_2$O | 1 | 1 | 1 | 1 | 1 | 1 | 1 |
| acetone | 1 | 3 | 3 | 3 | 2 | 3 | 2 |
| Cl—benzene | 2 | 3 | 4 | 3 | 3 | 4 | 3 |

*1 drop of the respective chemical left for 1 hour on the film:
1 = no attack
2 = slightly attacked
3 = severely attacked

EXAMPLES XV TO XXII (AND COMPARATIVE EXAMPLES 2+3)

The recipes of further curable mixtures for lacquers are summarised in Table 4. The mixing of the respective constituents is performed in the known manner. Whilst the solvent-free mixtures according to Examples XV to XVIII and comparative Example 2 can be produced and applied at room temperature, it is necessary according to Examples XIX to XXIII and comparative Example 3 to firstly dissolve the solid epoxide resin at about 60° C. in the solvent. After cooling to 20° C., the curing agent is added in the customary manner, and mixed in until the mixture is homogeneous. The lacquer can be subsequently applied.

The epoxide resins used in the tests are as follows:

resin A: this corresponds to the type used in Examples III to XIV;

resin B: a polyglycidyl ether which is solid at room temperature, which is produced by condensation of bisphenol A with epichlorohydrin in the presence of alkali, and which has an epoxide content of 2.1 epoxide equivalents/kg and a softening point of about 50° C. (Kofler).

As amine curing agents there are used, besides the product according to Examples 1 and 2, respectively, the following three adduct curing agents:

adduct curing agent M: pre-adduct, produced by reaction of 1 mol of resin A with 4 mols of the curing agent obtained according to Example 1 (viscosity at 25° C.: 4500 mPa s, amine content: 5.6 gram equiv./kg);

adduct curing agent N: pre-adduct, produced by reaction of 1 mol of resin A with 2.5 mols of the curing agent produced according to Example 10, in benzyl alcohol; the content of benzyl alcohol in the curing agent is 27% (viscosity at 25° C.: 3700 mPa s, amine content 3.6 gram equiv./kg);

adduct curing agent O: pre-adduct, produced by reaction of 1 mol of resin A with 3.5 mols of the curing agent produced according to Example 1; this product contains as accelerator 17% of bisphenol A (viscosity at 25° C.: 5900 mPa s, amine content 5.2 gram equiv./kg).

TABLE 4

(quantity values in parts by weight)

| Example | Resin A | Resin B | Curing agent according to Ex. 1 and 2 | 2,4,6-Tri-(dimethyl-aminomethyl) phenol | Adduct curing agent M | Adduct curing agent N | Adduct curing agent O | Xylene | Butanol | Comparison curing agent tri-methylhexamethylene-diamine |
|---|---|---|---|---|---|---|---|---|---|---|
| XV | 100 | | 34 | 2 | | | | | | |
| XVI | 100 | | | | 50 | | | | | |
| XVII | 100 | | | | | 90 | | | | |
| XVIII | 100 | | | | | | 50 | | | |
| XIX | | 100 | 14 | | | | | 40 | 10 | |
| XX | | 100 | 12 | 2 | | | | 40 | 10 | |
| XXI | | 100 | | | 21 | | | 44 | 11 | |
| XXII | | 100 | | | | 38 | | 48 | 12 | |
| XIII | | 100 | | | | | 21 | 44 | 11 | |
| comparative Example 2 | 100 | | | 2 | | | | | | 20 |
| comparative Example 3 | | 100 | | | | | | 36 | 9 | 8 |

The lacquer mixtures and the cured systems are tested according to the following specifications:

viscosity according to DIN 53015 at 25° C.;

gelling time of 100 ml at 20° C.: measurement is made by means of the Tecam device of Fa Techne (Cambridge) Ltd., Duxford Cambridge U.K.;

time to become bone dry and curing time, 200 μm film with solvent-free application, 50 μm film with solvent-containing application, measured by means of the Universal drying-time testing apparatus (Type 338) (Erichsen) at 20° C. with 65% relative humidity;

hardness according to Persoz at 20° C. with 65% relative humidity; recording of the hardness made in seconds; apparatus Type 300 (Erichsen); film thickness with solvent-free application 200 μm, with solvent-containing application 50 μm;

deep drawing property according to Erichsen, DIN 53152, measured at 20° C. with 65% relative humidity; solvent-free application 200 μm film thickness, solvent-containing application 50 μm film thickness; result given in mm;

impact test, impact applied to film: testing at 20° C. with 65% relative humidity; weight of the test hammer 1 kg; diameter of the striking hemisphere 2 cm; solvent-free application 200 μm film thickness: solvent-containing application 50 μm film thickness, result given in cmkg;

mandrel test, 15 mm mandrel (DIN 53 152) at 20° C. with 65% relative humidity; film-thickness with solvent-free application 200 μm, with solvent-containing application 50 μm.

The test results are summarised in Table 5.

TABLE 5

| Example No. | XV | XVI | XVII | XVIII | XIX | XX | XXI | XXII | XXIII | comparative Example 2 | comparative Example 3 |
|---|---|---|---|---|---|---|---|---|---|---|---|
| viscosity mPas | 600 | 5400 | 3300 | 6000 | 1500 | 1200 | 1600 | 1000 | 1700 | 700 | 2700 |
| gelling time h | 11:15 | 9:10 | 7:00 | 1:45 | 50 | 18 | 47 | 49 | 41 | 1:15 | 3 |
| time to become bone-dry h | 30 | 30 | 26 | 12 | 19 | 12 | 24 | 26 | 22 | 36 | 5 |
| curing time h | >30 | >30 | >30 | 20 | >30 | >30 | >30 | >30 | >30 | 6 | 8 |
| hardness accord. to Persoz 1 week 20° C.s | 350 | 300 | 200 | 360 | 80 | 110 | 90 | 80 | 70 | 330 | 150 |

TABLE 5-continued

| Example No. | XV | XVI | XVII | XVIII | XIX | XX | XXI | XXII | XXIII | comparative Example 2 | comparative Example 3 |
|---|---|---|---|---|---|---|---|---|---|---|---|
| Erichsen-test | | | | | | | | | | | |
| 1 week 20° C. mm | 3.0 | 6.0 | 9.5 | 5.5 | 9.5 | 9.5 | 9.5 | 9.5 | 9.5 | 1.0 | 7.0 |
| 1 week 60° C. mm | 6.0 | 5.0 | 8.5 | 3.0 | 9.0 | 9.5 | 9.0 | 9.5 | 9.5 | 5.0 | 5.5 |
| impact test | | | | | | | | | | | |
| 1 week 20° C. cmkg | 60 | 20 | 90 | 50 | 90 | 90 | 90 | 90 | 90 | 20 | 70 |
| 1 week 60° C. cmkg | 90 | 50 | 90 | 80 | 90 | 90 | 90 | 90 | 90 | 80 | 90 |
| mandrel test | | | | | | | | | | | |
| 1 week 20° C. ∠° | 10 | 20 | 180 | 20 | 180 | 180 | 180 | 180 | 180 | 10 | 90 |
| 1 week 60° C. ∠° | 180 | 30 | 180 | 70 | 180 | 180 | 180 | 180 | 180 | 90 | 180 |

What is claimed is:

1. A compound of the formula I

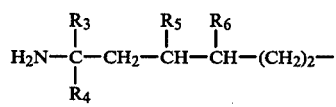

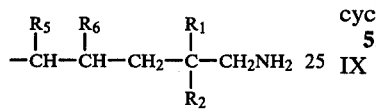 (I)

wherein
$R_1$ is alkyl having 1-12 C atoms,
$R_2$ is hydrogen or alkyl having 1-12 C atoms,
$R_3$ is alkyl having 1-12 C atoms or cycloalkyl having 4-12 ring C atoms,
$R_4$ is hydrogen, alkyl having 1-12 C atoms or cycloalkyl having 4-12 ring C atoms, or
either or both of $R_1$ and $R_2$; and $R_3$ and $R_4$ together are alkylene having 3-11 C atoms, and
$R_5$ and $R_6$ independently of one another are hydrogen or methyl.

2. A compound of the formula I according to claim 1 wherein $R_1$ is alkyl having 1-5 C atoms, $R_2$ is hydrogen or alkyl having 1-5 C atoms, $R_3$ is alkyl having 1-7 C atoms or cycloalkyl having 5-8 C atoms, $R_4$ is hydrogen or alkyl having 1-5 C atoms, or $R_1$ and $R_2$ together are alkylene having 4-7 C atoms, and $R_5$ and $R_6$ are each hydrogen.

3. A compound of the formula I according to claim 1, wherein $R_1$ is alkyl having 1-5 C atoms, $R_2$ is alkyl having 1-5 C atoms or hydrogen, or $R_1$ and $R_2$ together are alkylene having 4-7 C atoms, $R_3$ is branched-chain alkyl having 3-7 C atoms or cycloalkyl having 5-8 C atoms, and $R_4$, $R_5$ and $R_6$ are each hydrogen.

4. A compound of the formula I according to claim 1, wherein $R_1$ and $R_2$ are each methyl or ethyl, or together are $C_{4-7}$-alkylene, $R_3$ is isopropyl, 3-pentyl, $C_{5-8}$-cycloalkyl, and $R_4$, $R_5$ and $R_6$ are each hydrogen.

5. A compound according to claim 1 of the formula IX

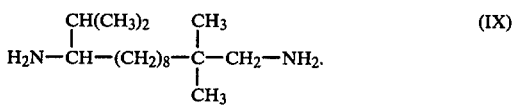 (IX)

6. A compound according to claim 1 of the formula X

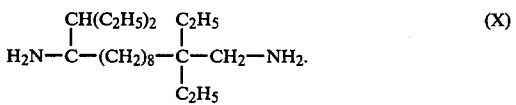 (X)

7. The compound according to claim 1 which is 1-cyclohexyl-10,10-pentamethylene-1,11-diaminoundecane.

8. The compound according to claim 1 which is 1,1,10-trimethyl-1,11-diaminoundecane.

* * * * *